(12) United States Patent
Dischert et al.

(10) Patent No.: US 10,774,320 B2
(45) Date of Patent: Sep. 15, 2020

(54) METHODS AND MICROORGANISMS FOR THE PRODUCTION OF GLYCOLIC ACID AND/OR GLYOXYLIC ACID

(71) Applicant: METABOLIC EXPLORER, Saint Beauzire (FR)

(72) Inventors: Wanda Dischert, Vic-le-Comte (FR); Gwenaëlle Corre, Saint Beauzire (FR); Philippe Soucaille, Deyme (FR)

(73) Assignee: METABOLIC EXPLORER, Saint Beauzire (FR)

(*) Notice: Subject to any disclaimer, the term of this patent is extended or adjusted under 35 U.S.C. 154(b) by 0 days.

(21) Appl. No.: 16/476,208

(22) PCT Filed: Jan. 26, 2018

(86) PCT No.: PCT/EP2018/051919
§ 371 (c)(1),
(2) Date: Jul. 5, 2019

(87) PCT Pub. No.: WO2018/138240
PCT Pub. Date: Aug. 2, 2018

(65) Prior Publication Data
US 2019/0367898 A1  Dec. 5, 2019

(30) Foreign Application Priority Data
Jan. 26, 2017  (EP) ..................... 17305084

(51) Int. Cl.
*C12P 7/42* (2006.01)
*C12N 9/88* (2006.01)
*C12N 9/04* (2006.01)
*C12P 7/40* (2006.01)

(52) U.S. Cl.
CPC ............ *C12N 9/88* (2013.01); *C12N 9/0006* (2013.01); *C12P 7/40* (2013.01); *C12P 7/42* (2013.01); *C12Y 101/03015* (2013.01); *C12Y 401/02009* (2013.01); *C12Y 401/02022* (2013.01)

(58) Field of Classification Search
CPC combination set(s) only.
See application file for complete search history.

(56) References Cited

U.S. PATENT DOCUMENTS

| 5,439,813 | A  | 8/1995  | Anton et al. |
| 7,439,391 | B2 | 10/2008 | Gallagher et al. |
| 2007/0026510 | A1 | 2/2007 | Iwasaki et al. |
| 2016/0002610 | A1 | 1/2016 | Kodama et al. |

FOREIGN PATENT DOCUMENTS

| CN | 105647844 A | 6/2016 |
| CN | 106011185 A | 10/2016 |
| EP | 2 025 759 A1 | 2/2009 |
| EP | 2 025 760 A1 | 2/2009 |
| EP | 2 980 215 A1 | 5/2016 |
| JP | 2007-228927 A | 9/2007 |
| WO | WO 94/20631 A2 | 9/1994 |
| WO | WO 94/28155 A1 | 12/1994 |
| WO | WO 95/01444 A1 | 1/1995 |
| WO | WO 96/00793 A1 | 1/1996 |
| WO | WO 99/54856 A1 | 10/1999 |
| WO | WO 2004/076659 A2 | 9/2004 |
| WO | WO 2005/106005 A1 | 11/2005 |
| WO | WO 2006/016705 A1 | 2/2006 |
| WO | WO 2006/069110 A2 | 6/2006 |
| WO | WO 2007/011939 A3 | 1/2007 |
| WO | WO 2007/140816 A1 | 12/2007 |
| WO | WO 2007/141316 A3 | 12/2007 |
| WO | WO 2009/042950 A1 | 4/2009 |
| WO | WO 2009/059096 A1 | 5/2009 |
| WO | WO 2009/059104 A1 | 5/2009 |
| WO | WO 2010/108909 A1 | 9/2010 |
| WO | WO 2011/036213 A2 | 3/2011 |
| WO | WO 2011/157728 A1 | 12/2011 |
| WO | WO 2012/025780 A1 | 3/2012 |
| WO | WO 2012/153041 A1 | 11/2012 |
| WO | WO 2012/153042 A1 | 11/2012 |
| WO | WO 2012/153043 A1 | 11/2012 |
| WO | WO 2013/001055 A1 | 1/2013 |
| WO | WO 20131050659 A1 | 4/2013 |
| WO | WO 2014/162063 A1 | 10/2014 |
| WO | WO 2016/044713 A1 | 3/2016 |
| WO | WO 2016/079440 A1 | 5/2016 |
| WO | WO 2016/193540 A1 | 12/2016 |

OTHER PUBLICATIONS

Brosius et al., "Spacing of the −10 and −35 Regions in the tac Promoter: Effect on Its in Vivo Activity". The Journal of Biological Chemistry, vol. 260, No. 6, 1985, pp. 3539-3541.

Carrier et al., "Library of Synthetic 5' Secondary Structures to Manipulate mRNA Stability in *Escherichia coli*", Biotechnol. Prog., vol. 15, 1999, pp. 58-64.

Cativiela et al., "Heterogeneous catalysis in the synthesis and reactivity of allantoin", Green Chemistry, vol. 5, Feb. 20, 2003, pp. 275-277.

Datsenko et al., "One-step inactivation of chromosomal genes in *Escherichia coli* K-12 using PCR products", Proc Nati Acad Sci, vol. 97, No. 12, Jun. 6, 2000, pp. 6640-6645.

(Continued)

*Primary Examiner* — Tekchand Saidha
(74) *Attorney, Agent, or Firm* — Birch, Stewart, Kolasch & Birch, LLP

(57) ABSTRACT

The present invention relates to methods and recombinant microorganisms useful for the production of glycolic acid and/or glyoxylic acid. The methods of the invention involve either only one step of fermentation of the modified microorganisms of the invention or one step of fermentation of the modified microorganisms of the invention and one step of either biological or chemical conversion of the glycolic acid or of the glyoxylic acid, the microorganism of the invention over expressing a phosphoketolase gene.

16 Claims, No Drawings

Specification includes a Sequence Listing.

(56) References Cited

OTHER PUBLICATIONS

Furukawa of al., "Chemoselective Conversion from α-Hydroxy Acids to α-Keto Acids Enabled by Nitroxyl-Radical-Catalyzed Aerobic Oxidation", Organic Letters, vol. 18, No. 17, Aug. 17, 2016, pp. 4230-4233.
Isobe et al., "A method for glyoxylic acid production using cells of *Alcaligenes* sp. GOX373", Journal of Biotechnology, vol. 75, 1999, pp. 265-271.
Jamil et al., "Mechanistic and Stereochemical Studies of Glycine Oxidase from Bacillus subtilis Strain R5", Biochemistry, vol. 49, No. 34, 2010, pp. 7377-7383.
Job et al., "Glycine Oxidase from Bacillus subtilis: Characterization of a New Flavoprotein", The Journal of Biological Chemistry, vol. 277, No. 9, 2002, pp. 6985-6993, 10 pages.
Kataoka et al., "Glycolic Acid Production Using Ethylene Glycol-Oxidizing Microorganisms", Biosci. Biotechnol. Biochem., vol. 65, No. 10, 2001, pp. 2265-2270.
Kovach et al., "Four new derivatives of the broad-host-range cloning vector pBBR1MCS, carrying different antibiotic-resistance cassettes", Gene, vol. 166, 1995, pp. 175-176.
Lerner et al., "Low copy number plasmids for regulated low-level expression of cloned genes in *Escherichia coli* with blue/white insert screening capability", Nucleic Acids Research, vol. 18, No. 15, 1990, p. 4631.
Loewen et al., "Purification and characterization of catalase HPII from *Escherichia coli* K12", Biochem. Cell. Biol., vol. 64, 1986, pp. 638-646.

Meile et al., "Characterization of the D-Xylulose 5-Phosphate/D-Fructose 6-Phosphate Phosphoketolase Gene (xfp) from Bifidobacterium lactis", Journal of Bacteriology, vol. 183, No. 9, May 2001, pp. 2929-2936.
Nishiya et al., "Purification and Characterization of a novel glycine oxidase from Bacillus subtilis", FEBS Letters, vol. 438, 1998, pp. 263-266.
Oshiro et al., "Kinetic modeling and sensitivity analysis of xylose metabolism in Lactococcus lactis IO-1", Journal of Bioscience and Bioengineering, vol. 108, No. 5, 2009; pp. 376-384.
Palmeros et al, "A family of removable cassettes designed to obtain antibiotic-resistance-free genomic modifications of *Escherichia coli* and other bacteria", Gene, vol. 247, 2000, pp. 255-264.
Papini et al., "Physiological characterization of recombinant *Saccharomyces cerevisiae* expressing the Aspergillus nidulans phosphoketolase pathway: validation of activity through C-based metabolic flux analysis", Appl Microbiol Biotechnol, vol. 95, 2012, pp. 1001-1010.
Posthuma et al., "Expression of the Xylulose 5-Phosphate Phosphoketolase Gene, xpkA, from Lactobacillus pentosus MD363 Is Induced by Sugars That Are Fermented via the Phosphoketolase Pathway and Is Repressed by Glucose Mediated by CcpA and the Mannose Phosphoenolpyruvate Phosphotransferase System", Applied and Environmental Microbiology, vol. 68, No. 2, Feb. 2002, pp. 831-837.
Racker, "Enzymes of Carbohydrate Metabolism", Methods Enzymol., vol. 5, 1962, pp. 276-280.
Sardari et al., "Semicarbazide-functionalized resin as a new scavenger for in situ recovery of 3-hydroxypropionaldehyde during biotransformation of glycerol by Lactobacillus reuteri", Journal of Biotechnology, vol. 192, 2014, pp. 223-230.
Schröter et al., "On the mechanism of phosphoketolase: Conversion of thiamine pyrophosphate activated glycolaaldehyde", Biochimica et Biophysica Acta, vol. 77, 1963, pp. 474-481.

METHODS AND MICROORGANISMS FOR THE PRODUCTION OF GLYCOLIC ACID AND/OR GLYOXYLIC ACID

FIELD OF THE INVENTION

The present invention relates to methods and recombinant microorganisms useful for the production of glycolic acid and/or glyoxylic acid. The microorganisms of the invention are modified in a way that the glycolic acid and/or glyoxylic acid yield on carbon source is increased by overexpressing phosphoketolase activity. The methods of the invention involve either only one step of fermentation of the modified microorganisms of the invention or one step of fermentation of the modified microorganisms of the invention and one step of either biological or chemical conversion of the glycolic acid or of the glyoxylic acid.

BACKGROUND OF THE INVENTION

Carboxylic acids are organic compounds that contain at least one carboxyl group. Carboxylic acids occur widely and include the amino acids (which make up proteins) and acetic acid (which is part of vinegar and occurs in metabolism) for instance. Carboxylic acids are used in the production of polymers, pharmaceuticals, solvents, and food additives. Industrially important carboxylic acids include acetic acid (component of vinegar, precursor to solvents and coatings), acrylic and methacrylic acids (precursors to polymers, adhesives), adipic acid (polymers), citric acid (beverages), ethylenediaminetetraacetic acid (EDTA) (chelating agent), fatty acids (coatings), maleic acid (polymers), propionic acid (food preservative), terephthalic acid (polymers), butyric acid (food additive), succinic acid (food additive, polymers).

Glycolic acid ($HOCH_2COOH$, CAS Number: 79-14-1), or glycolate for its conjugate base, is the simplest member of the alpha-hydroxy acid family of carboxylic acids. Glycolic acid has dual functionality with both alcohol and moderately strong acid functional groups on a very small molecule. Its properties make it ideal for a broad spectrum of consumer and industrial applications, including use in water well rehabilitation, leather industry, oil and gas industry, laundry and textile industry, cleaning products, and as a component in personal care products. It can also be used to produce a variety of polymeric materials, including thermoplastic resins comprising polyglycolic acid which have excellent gas barrier properties, and thus may be used to make packaging materials having the same properties (e.g., beverage containers, etc.). The polyester polymers gradually hydrolyze in aqueous environments at controllable rates. This property makes them useful in biomedical applications such as dissolvable sutures and in applications where a controlled release of acid is needed to reduce pH. Currently, more than 50,000 tons of glycolic acid are consumed annually worldwide.

Although glycolic acid occurs naturally as a trace component in sugarcane, beets, grapes and fruits, it is mainly synthetically produced. Other technologies to produce glycolic acid are described in the literature or in patent applications. For instance, EP 2025759 and EP 2025760 patent applications describe a method for producing the said hydroxycarboxylic acid from aliphatic polyhydric alcohol having a hydroxyl group at the end by using a microorganism. This method is a bioconversion, as is the one described by Michihiko Kataoka in the paper on the production of glycolic acid using ethylene glycol-oxidizing microorganisms (Kataoka et al., 2001). Glycolic acid is also produced by bioconversion from glycolonitrile using mutant nitrilases with improved nitrilase activity and that technique was disclosed in patent applications WO 2006/069110, WO 2009/059104, and WO 2009/059096, or by bioconversion from ethylene glycol, glycolaldehyde or glyoxal as disclosed in patent applications JP 2007/228927 or WO 2005/106005. Methods and microorganisms for producing glycolic acid by fermentation from renewable resources wherein carbohydrates are converted to glycolic acid by one direct step of fermentation were disclosed in patent applications WO 2007/141316, WO 2010/108909, WO 2011/036213, WO 2011/157728, WO 2012/025780, CN105647844A, CN106011185A, and WO 2016/079440 for methods using *Escherichia coli* strains, and in WO 2013/050659, WO 2014/162063, and WO 2016/193540 using *Saccharomyces cerevisiae* or *Kluyveromyces lactis* strains.

Glyoxylic acid or oxoacetic acid (HCOCOOH, CAS Number: 298-12-4) or glyoxylate for its conjugate base is a C2 carboxylic acid. Glyoxylic acid is an intermediate of the glyoxylate cycle, which enables organisms, such as bacteria, fungi and plants to convert fatty acids into carbohydrates. Glyoxylate is the byproduct of the amidation process in biosynthesis of several amidated peptides. It is a colourless solid that occurs naturally and is useful industrially. It is used as a cleaning agent for a variety of industrial applications, as a specialty chemical and biodegradable copolymer feedstock and as an ingredient in cosmetics. It is a useful compound for agricultural and pharmaceutical chemicals. Indeed, glyoxylic acid can be used in pharmaceutical industry since its condensation with phenols gives 4-hydroxymandelic acid which reacts with ammonia to give hydroxyphenylglycine, a precursor to the drug amoxicillin or which can be reduced to give 4-hydroxyphenylacetic acid, a precursor to the drug atenolol. Moreover acid-catalysed reaction of glyoxylic acid with urea leads to the production of allantoin used in cosmetics, ointments and in the treatment of some cancers (Cativiela et al., 2003). Finally, condensation with guaiacol in place of phenol provides a route to vanillin, used as a flavoring agent in foods, beverages, and pharmaceuticals.

Although glyoxylic acid occurs naturally as a trace component in unripe fruit and young green leaves, it is mainly synthetically produced. Other technologies to produce glyoxylic acid are described in the literature or in patent applications. For instance, glyoxylic acid may be chemically produced by heating dibromoacetic acid with some water or by electrolytic reduction of oxalic acid or by nitric oxidation of glyoxal. Some patent applications describe processes of production of glyoxylic acid by bioconversion, such as patent applications WO 1993/14214, U.S. Pat. No. 5,439,813, and WO 1994/28155 disclosing the bioconversion from glycolic acid using glycolate oxidase produced by a microorganism, as well as Isobe & Nishise (1999). Patent application US 2007/0026510 discloses the bioconversion from glyoxal using an aldehyde oxidase.

The industrial interest of glycolic acid and glyoxylic acid coupled with environmental concerns due to chemical by-products formed during chemical productions render microbial production of such carboxylic acids an attractive prospect.

The inventors have identified new methods for the production of glycolic acid and/or glyoxylic acid from carbohydrates as sole carbon source involving at least one fermentative step and a modified microorganism in which activity of phosphoketolase is enhanced.

Phosphoketolase activity and genes encoding enzymes with such activities are known in the art (Papini et al., 2012).

Two different phosphoketolase activities have been reported in bacteria. Xylulose 5-phosphate phosphoketolase catalyses the phosphate consuming conversion of xylulose 5-phosphate to glyceraldehyde 3-phosphate and acetylphosphate with release of water. Xylulose 5-phosphate phosphoketolase is, for instance, encoded by the xpkA gene from *Lactobacillus pentosus* (Posthuma et al., 2002). Fructose 6-phosphate phosphoketolase catalyses the phosphate consuming conversion of fructose 6-phosphate to erythrose 4-phosphate and acetylphosphate with release of water. Few genes encode phosphoketolases having both xylulose 5-phosphate phosphoketolase and fructose 6-phosphate phosphoketolase activities, as, for instance, is the case for the protein encoded by the gene xfp from *Bifidobacterium lactis* (Meile et al., 2001) or *Bifidobacterium animalis* (WO 2006/016705 and WO 2016/044713).

The use of phosphoketolase for the production of metabolites of interest is already known and has been disclosed in patent applications WO 2006/016705 and in WO 2016/044713. The metabolites of interest are glutamic acid, glutamine, proline, arginine, leucine, cysteine, succinate, polyhydrobutyrate and 1,4-butanediol. The use of phosphoketolase for the production of glycolic acid or glyoxylic acid has never been disclosed.

The methods and the microorganisms of the invention are new over the prior art since the use of phosphoketolase for the production of glycolic acid and/or glyoxylic acid has never been previously disclosed. The inventors have surprisingly found that the overproduction of phosphoketolase in the microorganisms of the invention improves the production of glycolic acid and/or glyoxylic acid.

The methods identified by the inventors involve either only one step of fermentation of the modified microorganisms of the invention or one step of fermentation of the modified microorganisms of the invention and one step of either biological or chemical conversion of the glycolic acid or of the glyoxylic acid.

SUMMARY OF THE INVENTION

The invention relates to recombinant microorganisms and methods for improving the production of glycolic acid and/or glyoxylic acid from carbohydrates as sole carbon source and using at least one step of fermentation and a modified microorganism wherein expression of at least one gene chosen among aceB, glcB, gcl and eda is attenuated and expression of a gene encoding xylulose 5-phosphate phosphoketolase and/or fructose 6-phosphate phosphoketolase is enhanced. Preferably the gene encoding the phosphoketolase is chosen among the xpkA gene from *Lactobacillus pentosus*, the xfp gene from *Bifidobacterium animalis*, or the xfp gene from *Bifidobacterium lactis*, or their homologous genes.

The methods identified by the inventors involve either only one step of fermentation of the modified microorganism of the invention for the production of glycolic acid or glyoxylic acid or one step of fermentation of the modified microorganism of the invention for the production of the corresponding intermediates glycolic acid or glyoxylic acid and one step of biological or chemical conversion of the intermediates glycolic acid or glyoxylic acid into glyoxylic acid or glycolic acid, respectively.

Another method of the invention relates to the production of glyoxylic acid from glycine using a glycine oxidase and optionally a catalase.

The microorganisms of the invention are chosen among bacteria such as Enterobacteriaceae, Clostridiaceae, Corynebacteriaceae, Bacillaceae, Bifidobacteriaceae, Lactobacillaceae or yeast. More preferably, the microorganisms of the invention are from the *Escherichia coli* species.

DETAILED DESCRIPTION OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety.

Furthermore, the practice of the present invention employs, unless otherwise indicated, conventional microbiological and molecular biological techniques within the skill of the art. Such techniques are well known to the skilled worker, and are explained fully in the literature.

It must be noted that as used herein and in the appended claims, the singular forms "a," "an," and "the" include plural reference unless the context clearly dictates otherwise. Thus, for example, a reference to "a microorganism" includes a plurality of such microorganisms, and a reference to "an endogenous gene" is a reference to one or more endogenous genes, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In the claims that follow and in the consecutive description of the invention, except where the context requires otherwise due to express language or necessary implication, the word "comprise," "contain," "involve," or "include" or variations such as "comprises," "comprising," "containing," "involved," "includes," "including" are used in an inclusive sense, i.e. to specify the presence of the stated features but not to preclude the presence or addition of further features in various embodiments of the invention.

The invention relates to recombinant microorganisms and methods for improving the production of glycolic acid and/or glyoxylic acid. The methods identified by the inventors involve either only one step of fermentation of the modified microorganism of the invention for the production of glycolic acid or glyoxylic acid or one step of fermentation of the modified microorganism of the invention for the production of the corresponding intermediates glycolic acid or glyoxylic acid and one step of bioconversion of the intermediates into, respectively, glyoxylic acid or glycolic acid.

The term "glycolic acid" designates the carboxylic acid with chemical formula HOCH2COOH, and CAS Number 79-14-1.

The term "glyoxylic acid" designates the carboxylic acid with chemical formula HCOCOOH, and CAS Number: 298-12-4.

The term "microorganism," as used herein, refers to a bacterium, yeast or fungus which is not modified artificially. Preferentially, the microorganism is selected among Enterobacteriaceae, Clostridiaceae, Corynebacteriaceae, Bacillaceae, Bifidobacteriaceae, Lactobacillaceae or yeast. More preferentially, the microorganism is a species of *Escheri-* chia, *Klebsiella, Lactobacillus, Bifidobacterium, Corynebacterium, Kluyveromyces* or *Saccharomyces*. Even more preferentially, the microorganism of the invention is from *Escherichia coli* species.

The term "recombinant microorganism" or "genetically modified microorganism," as used herein, refers to a bacterium, yeast or fungus that is not found in nature and is genetically different from its equivalent found in nature. It means it is modified either by introduction or by deletion or by modification of genetic elements. It can also be transformed by forcing the development and evolution of new metabolic pathways by combining directed mutagenesis and evolution under specific selection pressure (see, for example, WO 2004/076659 or WO 2007/011939).

A microorganism may be modified to express exogenous genes if these genes are introduced into the microorganism with all of the elements allowing their expression in the host microorganism. The modification or "transformation" of microorganisms with exogenous DNA is a routine task for those skilled in the art.

A microorganism may be modified to modulate the expression level of an endogenous gene.

The term "endogenous gene" means that the gene was present in the microorganism before any genetic modification. Endogenous genes may be overexpressed by introducing heterologous sequences in addition to, or to replace, endogenous regulatory elements, or by introducing one or more supplementary copies of the gene into the chromosome or a plasmid. Endogenous genes may also be modified to modulate their expression and activity of the corresponding encoded protein. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, down regulate and/or lower the activity of the endogenous gene product.

Another way to modulate their expression is to exchange the endogenous promoter of a gene (e.g., wild type promoter) with a stronger or weaker promoter to up or down regulate expression of the endogenous gene. These promoters may be homologous or heterologous. It is well within the ability of the person skilled in the art to select appropriate promoters.

Contrariwise, "exogenous gene" means that the gene was introduced into a microorganism, by means well-known to the man skilled in the art whereas this gene is not naturally occurring in the microorganism. Exogenous genes may be integrated into the host chromosome, or be expressed extra-chromosomally by plasmids or vectors. A variety of plasmids, which differ with respect to their origin of replication and their copy number in the cell, are well-known in the art. These genes may be homologous.

In the context of the invention, the term "homologous gene" is not limited to designate genes having a theoretical common genetic ancestor, but includes genes which may be genetically unrelated that have, none the less, evolved to encode protein which perform similar functions and/or have similar structure. Therefore, the term 'functional homologue" for the purpose of the present invention relates to the fact that a certain enzymatic activity may not only be provided by a specific protein of defined amino acid sequence, but also by proteins of similar sequence from other (un)related microorganisms.

Using the references given in Genbank for known genes, those skilled in the art are able to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerate probes to clone the corresponding gene in another organism. These routine methods of molecular biology are well known to those skilled in the art.

The terms "improved glycolic acid and/or glyoxylic acid production," "improve glycolic acid and/or glyoxylic acid production" and grammatical equivalents thereof, as used herein, refer to an increased glycolic acid and/or glyoxylic acid/carbon source yield (ratio of gram/mol glycolic acid and/or glyoxylic acid produced per gram/mol carbon source consumed that it can be expressed in percent). Methods for determining the amount of carbon source consumed and of glycolic acid and/or glyoxylic acid produced are well-known to those in the art. The yield is higher in the recombinant microorganism compared to the corresponding unmodified microorganism.

The terms "microorganism optimised for the fermentative production of glycolic acid and/or glyoxylic acid" refers to microorganisms evolved and/or genetically modified to present an improved glycolic acid and/or glyoxylic acid production in comparison with the endogenous production of the corresponding wild-type microorganism. Such microorganisms "optimised" for glycolic acid and/or glyoxylic acid production are well-known in the art, and have been disclosed in particular in patent applications WO 2007/141316, WO 2010/108909, WO 2011/036213, WO 2011/157728, and WO 2012/025780.

According to the invention the terms "fermentative production," "culture," "fermentation step," or "fermentation" are used to denote the growth of bacteria. This growth is generally conducted in fermenters with an appropriate culture medium adapted to the microorganism being used and containing at least one simple carbon source, and if necessary co-substrates.

An "appropriate culture medium" designates a medium (e.g., a sterile, liquid media) comprising nutrients essential or beneficial to the maintenance and/or growth of the cell such as carbon sources or carbon substrates, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids and vitamins.

The term "carbon source" or "carbon substrate" or "source of carbon" according to the present invention denotes any source of carbon that can be used by those skilled in the art to support the normal growth of a microorganism. The carbon source is chosen among carbohydrates which designate monosaccharides (such as glucose, galactose, xylose, fructose or lactose), oligosaccharides, disaccharides (such as sucrose, cellobiose or maltose), molasses, starch or its derivatives, hemicelluloses and combinations thereof. An especially preferred simple carbon source is glucose. Another preferred simple carbon source is sucrose. The carbon source can be derived from renewable feed-stock. Renewable feed-stock is defined as raw material required for certain industrial processes that can be regenerated within a brief delay and in sufficient amount to permit its transformation into the desired product. Vegetal biomass treated or not, is an interesting renewable carbon source.

According to the invention the terms "bioconversion step" or "bioconversion" or "biotransformation" or "bio catalysis" or "biological conversion" refer to the conversion of organic materials into desired products by a specific enzyme produced by an enzyme producer microorganism (different from the modified microorganisms of the invention). The reaction of bioconversion can be performed differently according to the enzyme, its mechanism and the constraint of the process and they are known by the man in the art:

1. The organic material may be contacted with the enzyme by adding to organic material the purified enzyme or,
2. The organic material may be contacted with the enzyme by adding to organic material the fermentation broth of the enzyme producer microorganism containing the enzyme cleared from the bacteria or,
3. The organic material may be contacted with the enzyme by adding to organic material the extract of lysed cells of the enzyme producer microorganism or,
4. The organic material may be contacted with the enzyme by adding to organic material the living cells of the enzyme producer microorganism previously treated to permit both the enzymatic reaction and the viability of said enzyme producer microorganism required for the reaction regeneration (specific cofactor availability). This system is called the whole-cell biocatalyst system.

In a preferred embodiment of the invention, the organic material originates from the first step of fermentation of the method of the invention that is to say glycolic acid or glyoxylic acid produced by the modified microorganisms of the invention. The organic material originating from the first step of fermentation can be more or less purified from the culture broth. In another embodiment of the invention, the organic material is the glycine which is chemically or biologically provided.

In a first aspect of the invention, the invention relates to a method for the production of glycolic acid and/or glyoxylic acid from carbohydrate as sole carbon source using at least one step of fermentation and a modified microorganism wherein the modified microorganism of the invention comprises attenuation of expression of at least one gene chosen among aceB, glcB, gcl and eda, and overexpression of at least one gene encoding xylulose 5-phosphate phosphoketolase and/or fructose 6-phosphate phosphoketolase.

As disclosed in patent application WO 2007/141316, deletion of at least one gene chosen among aceB encoding malate synthase, glcB encoding malate synthase, gcl encoding glyoxylate carboligase and eda encoding 2-keto-3-deoxygluconate 6-phosphate aldolase leads to a decrease of the conversion of glyoxylate allowing such accumulation of glyoxylate which could be recovered from the culture medium or could be further converted into glycolic acid. Preferably, in the microorganism of the invention expression of the genes aceB and glcB and gcl are attenuated.

More preferably, the modified microorganisms of the invention may be further modified as disclosed in patent applications WO 2010/108909, WO 2011/036213, WO 2011/157728, WO 2012/025780 with:

attenuation of the genes glcDEFG encoding glycolate oxidase and/or aldA encoding glycolaldehyde dehydrogenase leading to the inability to substantially metabolize glycolate increase of the glyoxylate pathway flux, obtained in particular by the attenuation of the genes icd encoding isocitrate dehydrogenase, aceK encoding Icd kinase-phosphatase, pta encoding phospho-transacetylase, ackA encoding acetate kinase, poxB encoding pyruvate oxidase, iclR or fadR encoding glyoxylate pathway repressors, and/or by the overexpression of the gene aceA encoding isocitrate lyase, Decreasing the level of isocitrate dehydrogenase can be accomplished by introducing artificial promoters that drive the expression of the icd gene, coding for the isocitrate dehydrogenase, or by introducing mutations into the icd gene that reduce the enzymatic activity of the protein.

Since the activity of the protein Icd is reduced by phosphorylation, it may also be controlled by introducing mutant aceK genes that have increased kinase activity or reduced phosphatase activity compared to the wild type AceK enzyme.

increase of the availability of NADPH, obtained in particular by the attenuation of the genes pgi, udhA, edd.

The terms "attenuation" or "expression attenuated" mean in this context that the expression of a gene and/or the production of an enzyme is decreased or suppressed compared to the non-modified microorganism leading to a decrease in the intracellular concentration of a ribonucleic acid, a protein or an enzyme compared to the non-modified microorganism. The man skilled in the art knows different means and methods to measure ribonucleic acid concentration or protein concentration in the cell including, for instance, use of Reverse Transcription Polymerase Chain Reaction (RT-PCR) to determine ribonucleic acid concentration and use of specific antibody to determine concentration of specific protein.

Decrease or suppression of the production of an enzyme is obtained by the attenuation of the expression of gene encoding said enzyme.

Attenuation of genes may be achieved by means and methods known to the man skilled in the art. Generally, attenuation of gene expression may be achieved by:

Mutating the coding region or the promoter region or,
Deleting all or a part of the promoter region necessary for gene expression or,
Deleting all or a part of the coding region of the gene by homologous recombination or,
Inserting an external element into the coding region or into the promoter region or,
Expressing the gene under the control of a weak promoter or an inducible promoter.

The man skilled in the art knows a variety of promoters exhibiting different strengths and which promoter to use for a weak or an inducible genetic expression.

The term "activity" of an enzyme is used interchangeably with the term "function" and designates, in the context of the invention, the reaction that is catalysed by the enzyme. The man skilled in the art knows how to measure the enzymatic activity of said enzyme.

The terms "attenuated activity" or "reduced activity" of an enzyme mean either a reduced specific catalytic activity of the protein obtained by mutation in the amino acids sequence and/or decreased concentrations of the protein in the cell obtained by mutation of the nucleotide sequence or by deletion of the coding region of the gene.

The terms "enhanced activity" or "increased activity" of an enzyme designate either an increased specific catalytic activity of the enzyme, and/or an increased quantity/availability of the enzyme in the cell, obtained for example by overexpressing the gene encoding the enzyme.

The terms "increased expression," "enhanced expression," or "overexpression" and grammatical equivalents thereof, are used interchangeably in the text and have a similar meaning. These terms mean that the expression of a gene or the production of an enzyme is increased compared to the non-modified microorganism leading to an increase in the intracellular concentration of a ribonucleic acid, a protein or an enzyme compared to the non-modified microorganism. The man skilled in the art knows different means and methods to measure ribonucleic acid concentration or protein concentration in the cell including, for instance, use of Reverse Transcription Polymerase Chain Reaction (RT-PCR) to determine ribonucleic acid concentration and use of specific antibody to determine concentration of specific protein.

Increased production of an enzyme is obtained by increasing expression of the gene encoding said enzyme.

To increase the expression of a gene, the man skilled in the art knows different techniques such as:

Increasing the number of copies of the gene in the microorganism. The gene is encoded chromosomally or extrachromosomally. When the gene is located on the chromosome, several copies of the gene can be introduced on the chromosome by methods of recombination, known by the expert in the field (including gene replacement). When the gene is located extra-chromosomally, it may be carried by different types of plasmids that differ with respect to their origin of replication and thus their copy number in the cell. These plasmids are present in the microorganism in 1 to 5 copies, or about 20 copies, or up to 500 copies, depending on the nature of the plasmid: low copy number plasmids with tight replication (pSC101, RK2), low copy number plasmids (pACYC, pRSF1010) or high copy number plasmids (pSK bluescript II).

Using a promoter leading to a high level of expression of the gene. The man skilled in the art knows which promoters are the most convenient. For example, promoters Ptrc, Ptac, Plac, or the lambda promoters PR and PL are widely used. These promoters can be "inducible" by a particular compound or by a specific external condition like temperature or light. These promoters may be homologous or heterologous.

Attenuating the activity or the expression of a transcription repressor, specific or non-specific of the gene.

Using elements stabilizing the corresponding messenger RNA (Carrier and Keasling, 1999) or elements stabilizing the protein (e.g., GST tags, GE Healthcare).

The terms "encoding" or "coding" refer to the process by which a polynucleotide, through the mechanisms of transcription and translation, produces an amino acid sequence. The gene(s) encoding the enzyme(s) can be exogenous or endogenous.

The term "phosphoketolase" typically refers to enzymes with xylulose 5-phosphate phosphoketolase activity (EC 4.1.2.9) and/or fructose 6-phosphate phosphoketolase activity (EC 4.1.2.22). Xylulose 5-phosphate phosphoketolase activity means the activity of phosphate-consuming conversion of xylulose 5-phosphate to glyceraldehyde 3-phosphate and acetylphosphate with release of water. Fructose 6-phosphate phosphoketolase activity means the activity of phosphate-consuming conversion of fructose 6-phosphate to erythrose 4-phosphate and acetylphosphate with release of water. These two activities may be measured with the method described by Meile et al (2001). D-xylulose 5-phosphate phosphoketolase enzyme or its encoding gene may originate from bacteria having an activity of D-xylulose 5-phosphate phosphoketolase, including lactic acid bacterium, methanol-assimilating bacterium, methane-assimilating bacterium, *Streptococcus* bacterium, and more specifically bacteria belonging to the genera *Acetobacter, Bifidobacterium, Lactobacillus, Thiobacillus, Streptococcus, Methylococus, Butyrivibrio, Fibrobacter*, and/or yeast belonging to the genera *Candida, Rhodotorula, Rhodosporidium, Pichia, Yarrowia Hansenula, Kluyveromyces Saccharomyces, Trichosporon, Wingea* or the like. Fructose 6-phosphate phosphoketolase enzyme or its encoding gene may originate from bacteria having an activity of fructose 6-phosphate phosphoketolase that belong to the genera *Acetobacter, Bifidobacterium, Chlorobium, Brucella, Methylococus, Gardnerella*, and/or yeast belonging to *Rhodotorula, Candida, Saccharomyces* or the like. Moreover, it has been reported that some enzymes catalyse both activities of xylulose 5-phosphate phosphoketolase and fructose 6-phosphate phosphoketolase, such as Xfp from *Bifidobacterium animalis* (WO 2006/016705 and WO 2016/044713) or from *Bifidobacterium lactis* (Meile et al., 2001).

In the context of the invention, the modified microorganisms overexpress phosphoketolase encoding gene so as to enhance the production of glycolic acid and/or glyoxylic acid. If the microorganisms of the invention naturally express phosphoketolase, the gene(s) encoding phosphoketolase(s) are overexpressed using overexpression methods detailed above. On the contrary, if the microorganism of the invention does not naturally express phosphoketolase, exogenous phosphoketolase encoding gene is introduced into the microorganism. In this case the introduction of the gene leads to an overexpression of the phosphoketolase encoding gene.

Phosphoketolase encoding genes are chosen among: xfp gene from *Bifidobacterium animalis* (WO 2006/016705 and WO 2016/044713), xfp gene from *Bifidobacterium lactis* (Meile et al., 2001), xpkA from *Lactobacillus pentosus* (Posthuma et al., 2002) or their homologous genes: xpk1 gene from *Lactobacillus plantarum*, xpk2 gene from *Lactobacillus plantarum*, xpk gene from *Streptococcus agalactiae* NEM316, ptk gene from *Lactococcus lactis* subsp. *lactis*, xpk gene from *Lactobacillus johnsonii*, xpk gene from *Lactobacillus acidophilus*, xfp gene from *Bifidobacterium longum*, xfp gene from *Chlorobium tepidum*, xfp gene from *Brucella suis*, xfp gene from *Brucella abortus*. Preferentially, the microorganism overexpresses xfp gene from *Bifidobacterium lactis* (Meile et al., 2001), xfp gene from *Bifidobacterium animalis* (WO 2006/016705 and WO 2016/044713), or xpkA from *Lactobacillus pentosus* (Posthuma et al., 2002). Even more preferably, the microorganism overexpresses the xfp gene from *Bifidobacterium animalis* (WO 2006/016705 and WO 2016/044713) or the xpkA gene from *Lactobacillus pentosus* (Posthuma et al., 2002).

In a preferred embodiment of the invention, the modified microorganism further overexpresses ycdW or its homologous genes in order to increase the conversion of glyoxylic acid into glycolic acid as disclosed in patent application WO 2007/141316. It is an object of the invention to provide a method for the production of glycolic acid using a modified microorganism in which the expression of at least one gene chosen among aceB, glcB, gcl and eda is attenuated, the expression of xfp gene from *Bifidobacterium lactis*, xfp gene from *Bifidobacterium animalis*, or xpkA from *Lactobacillus pentosus* and the expression of ycdW gene and/or yiaE gene are overexpressed. Preferably, in the method for the production of glycolic acid using a modified microorganism, the expression of at least one gene chosen among aceB, glcB, gcl and eda is attenuated, the expression of the xfp gene from *Bifidobacterium animalis* or the xpkA gene from *Lactobacillus pentosus* is overexpressed, and the expression of the ycdW gene and/or the yiaE gene is overexpressed.

This method for production of glycolic acid allows the production of glyoxylic acid by either biological or chemical conversion from glycolic acid. This second method of the invention comprises the step of optional isolation of glycolic acid from fermentation broth, conversion of glycolic acid into glyoxylic acid either by bioconversion using a glycolate oxidase encoded by the gene gldDEFG from *Escherichia coli* and a catalase encoded by the genes katE or katG from *Escherichia coli* (Loewen & Switala, 1986) or by chemical conversion for example using a nitroxyl radical catalyst such as AZADO (Furukawa et al., 2016) and recovering glyoxylic acid from conversion medium.

The optional isolation of glycolic acid may lie at least in the withdrawal of the microbial cells from the fermentation broth. Glycolic acid may be further purified from the other organic species from the fermentation broth as disclosed in patent applications WO2012/153041, WO2012/153042 and WO2012/153043 by successive distillations. Alternatively, glycolic acid may be purified by iterative crystallization steps as disclosed in U.S. Pat. No. 7,439,391 or by liquid-liquid extraction using adequate solvent. Usable solvents are well-known by the man in the art, whom is able to choose the most convenient solvent. Another way to purify glycolic acid from the fermentation broth is the use of fermentative extraction process also known as reactive extraction process or extractive fermentation process. Extractive fermentation could be considered as an integrated process, in which a reaction process i.e. fermentation, is combined with a purification operation, i.e. liquid extraction as disclosed in patent applications WO 2009/042950 or WO 1999/54856. The process presents the advantage of allowing the removal of glycolic acid as soon as it is produced, reducing the inhibition of cell growth due to the toxic effect of glycolic acid, and thus to produce and recover glycolic acid in one continuous step, thereby reducing the downstream processing and the recovery costs. The solvent is chosen among carbon-bonded oxygen-bearing solvents or phosphorus-bonded oxygen-bearing solvents or high-molecular weight aliphatic amines. Preferred solvents are tri-n-octyl phosphine oxide, tri-n-butyl phosphate, lauryl-trialkylmethylamine, tri-n-octylamine, tri-iso-octylamine, tri-n-(octyl-decyl)-amine, quaternary alkylammonium salt, polyethylene glycols, polyethyleneimine and polypropyleneimine. More preferentially, the solvent used is tri-n-octyl phosphine oxide. Advantageously, extractive fermentation may be completed by a subsequent step of crystallization or distillation.

The step of bioconversion of glycolic acid into glyoxylic acid is mediated by a glycolate oxidase also known as (S)-2-hydroxy-acid oxidase (EC number: 1.1.3.15) which catalyses the reaction:

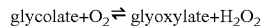
$$glycolate + O_2 \rightleftharpoons glyoxylate + H_2O_2$$

This enzyme belongs to the family of oxidoreductases, specifically those acting on the CH—OH group of the donor with oxygen as the acceptor.

The glycolate oxidase used in this invention may correspond to any naturally occurring form of the enzyme or any variant of these naturally enzymes which exhibit better stability or catalytic efficiency. The naturally occurring glycolate oxidase used may be extracted and purified from spinach or beet leaves or, alternatively, the gene encoding these enzymes may be inserted in a producer microorganism as disclosed in patent applications WO 1994/20631 and WO 1995/01444. Alternatively, the gldDEFG genes from *Escherichia coli* encoding glycolate oxidase are overexpressed in a producer organism. The producer organism is chosen among *Pichia pastoris, Hansenula polymorpha, Aspergillus nidulans* or *Escherichia coli*. Most preferably, *Escherichia coli* is used. As glycolate oxidase generates $H_2O_2$, it is advantageous to use in combination with the glycolate oxidase a catalase (EC Number: 1.11.1.6) which is endogenously expressed by *Pichia pastoris, Hansenula polymorpha, Aspergillus nidulans* or *Escherichia coli*. In *Escherichia coli*, catalase is encoded by katE or katG genes. Preferably, glycolate oxidase and catalase are overexpressed in the same microorganism. Use of glycolate oxidase and catalase is disclosed in patent applications WO 1996/00793, WO 1994/20631 or in WO 1995/01444.

For the bioconversion, the glycolate oxidase and/or catalase are contacted with the glycolic acid by adding directly the purified enzymes to the solution of glycolic acid (partially purified or not) or adding the fermentation broth of the glycolate oxidase and/or catalase producer microorganism or an extract of lysed cell of the glycolate oxidase and/or catalase producer microorganism. To improve efficiency of bioconversion, immobilized enzymes may be used after their purification as disclosed in U.S. Pat. No. 5,439,813.

Glyoxylic acid formed is then purified using means well known by the man skilled in the art as for instance crystallization or precipitation with calcium hydroxide or liquid-liquid extraction.

In another preferred embodiment of the invention, the modified microorganism is further engineered so as to attenuate expression of at least ycdW genes in order to avoid the conversion of glyoxylic acid into glycolic acid. It is also an object of the invention to provide a method for the production of glyoxylic acid using a modified microorganism in which the expression of at least one gene chosen among aceB, glcB, gcl and eda is attenuated, the expression of xfp gene from *Bifidobacterium lactis*, the expression of xfp gene from *Bifidobacterium animalis*, or xpkA gene from *Lactobacillus pentosus* are overexpressed and the expression of ycdW gene and yiaE gene are attenuated or completely abolished. Preferably, in the method for the production of glyoxylic acid using a modified microorganism, the expression of at least one gene chosen among aceB, glcB, gcl and eda is attenuated, and the expression of the xfp gene from *Bifidobacterium animalis* or the xpkA gene from *Lactobacillus pentosus* is overexpressed, and the expression of the ycdW gene and the yiaE gene are attenuated or completely abolished.

This method for production of glyoxylic acid allows the production of glycolic acid by either biological or chemical conversion from glyoxylic acid. This fourth method of the invention comprises the step of optional isolation of glyoxylic acid from fermentation broth, conversion of glyoxylic acid into glycolic acid either by bioconversion using a glyoxylate reductase or by chemical conversion using, for example, sodium borohydride and recovering glycolic acid from conversion medium. Said glyoxylate reductase can be encoded by the gene ycdW from *Escherichia coli* or by the gene grxA from *Rhizobium etli*.

The optional isolation of glyoxylic acid may lie at least in the withdrawal of the microbial cells from the fermentation broth. Glyoxylic acid may be further purified from the other organic species from the fermentation broth by ion exchange or by precipitation/crystallization methods or by liquid-liquid extraction. Another way to purify glyoxylic acid from the fermentation broth is the use of extractive fermentation process. Extractive fermentation could be considered as an integrated process, in which a reaction process i.e. fermentation, is combined with a purification operation, i.e. liquid extraction as disclosed in patent applications WO 2009/

042950 or WO 1999/54856. The process presents the advantage of allowing the removal of glyoxylic acid as soon as it is produced, reducing the inhibition of cell growth due to the toxic effect of glyoxylic acid, and thus to produce and recover glyoxylic acid in one continuous step, thereby reducing the downstream processing and the recovery costs. The solvent is chosen among carbon-bonded oxygen-bearing solvents or phosphorus-bonded oxygen-bearing solvents or high-molecular weight aliphatic amines. Preferred solvents are tri-n-octyl phosphine oxide, tri-n-butyl phosphate, lauryl-trialkylmethylamine, tri-n-octylamine, tri-iso-octylamine, tri-n-(octyl-decyl)-amine, quaternary alkylammonium salt, polyethylene glycols, polyethyleneimine and polypropyleneimine. More preferentially, the solvent used is tri-n-octyl phosphine oxide. Advantageously, extractive fermentation may be completed by a subsequent step of crystallization or distillation. Alternatively, to the extractive fermentation, to decrease toxicity of glyoxylic acid produced during fermentation, it is possible to add in the fermentation broth a molecule known to form a complex with aldehydes such as semicarbazide, or carbohydrazide or 2,4-dinitrophenylhydrazine so as to complex with glyoxylic acid and thus reduce toxicity of the aldehyde for the cells. This could allow for an improved productivity of glyoxylic acid (Sardari et al., 2014).

The step of bioconversion of glyoxylic acid into glycolic acid is mediated by a glyoxylate reductase. Glyoxylate reductase was first isolated from spinach leaves and is an enzyme that catalyses the reduction of glyoxylic acid to glycolic acid, using the cofactor NADH or NADPH. Glycolate reductase may be NADH dependent (EC Number: 1.1.1.26) or NADPH dependent (EC Number: 1.1.1.79). Examples of NADH dependent glyoxylate reductases which could be used are: GxrA encoded by gxrA gene from *Rhizobium etli*, GOR1 encoded by GOR1 gene from *Saccharomyces cerevisiae*, HprA encoded by hprA gene from *Methylobacterium extorquens* or GyaR encoded by gyaR gene from *Pyrococcus furiosus*. Examples of NADPH dependent glyoxylate reductases are: YcdW encoded by ycdW gene from *Escherichia coli*, YiaE encoded by yiaE gene from *Escherichia coli*, YjbG encoded by yjgB gene from *Escherichia coli*, YafB encoded by yafB gene from *Escherichia coli*, YqhD encoded by yqhD gene from *Escherichia coli* or GLYR1 and GLYR2 encoded by GLYR1 and GLYR2 genes from *Arabidopsis thaliana* . . . . Advantageously, the glyoxylate reductase producer microorganism is *Escherichia coli*.

For the bioconversion of glyoxylic acid into glycolic acid, the glyoxylate reductase enzymes require either NADH or NADPH cofactors. In such a case, the bioconversion needs to be done in presence of the specific enzyme and living cells able to produce and regenerate the cofactors during the reaction. This is a so called whole-cell biocatalyst system. A solution of glyoxylic acid partially purified or not is therefore contacted with the fermentation broth of the glyoxylate reductase producer microorganism having overproduced the glyoxylate reductase enzyme and being still viable in order to produce and regenerate the cofactors. To improve efficiency of bioconversion, immobilized enzymes may be used but still in presence of a living microorganism pre-treated in order to help the reaction.

Glycolic acid formed is then purified using means well-known by the man skilled in the art such as distillation, crystallization, precipitation with calcium hydroxide or liquid-liquid extraction.

In another embodiment of the invention, glyoxylic acid may be produced by bioconversion of glycine (CAS Number: 56-40-6) by using a glycine oxidase. Glycine oxidase (EC Number: 1.4.3.19) catalyses the reaction:

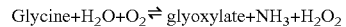

$$\text{Glycine} + H_2O + O_2 \rightleftharpoons \text{glyoxylate} + NH_3 + H_2O_2$$

The glycine oxidase used in this invention may correspond to any naturally occurring form of the enzyme or any variant of these naturally enzymes which exhibit better stability or catalytic efficiency as disclosed in patent application US 2016/0002610. Glycine oxidase has been identified in *Bacillus subtilis* (Nishiya & Imanaka, 1998; Job et al., 2002). This enzyme may be extracted and purified from *Bacillus subtilis* or, alternatively, the gene encoding this enzyme may be inserted in a producer microorganism. The producer organism is preferably *Escherichia coli*. As glycine oxidase generates $H_2O_2$, it is advantageous to use, in combination with the glycine oxidase, a catalase (EC Number: 1.11.1.6) which is endogenously expressed by *Escherichia coli* by katE and katG genes. Preferably, glycine oxidase and catalase are overexpressed in the same microorganism.

For the bioconversion, the glycine oxidase and/or catalase are contacted with glycine by adding the purified enzymes directly to the solution of glycine or by adding the fermentation broth of the glycine oxidase and/or catalase producer microorganism or an extract of lysed cell(s) of the glycine oxidase and/or catalase producer microorganism. To improve efficiency of bioconversion, immobilized enzymes may be used after their purification as disclosed in U.S. Pat. No. 5,439,813.

Finally, the invention relates to a microorganism modified for the production of glycolic acid and/or glyoxylic acid wherein expression of at least one gene chosen among aceB, glcB, gcl and eda is attenuated and expression of at least one gene encoding phosphoketolase is enhanced. The phosphoketolase is encoded by xfp gene from *Bifidobacterium animalis*, xfp gene from *Bifidobacterium lactis*, or xpkA gene from *Lactobacillus pentosus*.

For the production of glycolic acid, the microorganism of the invention is further modified to overexpress ycdW gene from *Escherichia coli* or at least one of its homologous genes.

For the production of glyoxylic acid, the microorganism of the invention is further modified to attenuate or completely abolish the expression of at least the gene ycdW.

The microorganism of the invention is chosen among Enterobacteriaceae, Clostridiaceae, Corynebacteriaceae, Bacillaceae, Bifidobacteriaceae, Lactobacillaceae, or yeast. More preferentially, the microorganism of the invention is from the *Escherichia coli* species.

EXAMPLES

The following experiments demonstrate how to produce glycolic acid or glyoxylic acid, using a modified glycolic acid producer *E. coli* recombinant strain as background.

In the examples given below, methods well-known in the art were used to construct *E. coli* strains containing replicating vectors and/or various chromosomal insertions, deletions, and substitutions using homologous recombination, as is well-described by Datsenko & Wanner, (2000).

Protocols

Several protocols have been used to construct the glyoxylic acid producing strains described in the following examples.

Protocol 1 (Chromosomal modifications by homologous recombination, selection of recombinants and antibiotic cassette excision flanked by FRT sequences) and protocol 2

(Transduction of phage P1) used in this invention have been fully described in patent application WO 2013/001055.

Protocol 3: Antibiotic cassette excision flanked by LoxP sequences

The resistance genes flanked by LoxP sequences were removed by using plasmid pJW168 (Palmeros et al., 2000) carrying gene coding for the Cre recombinase. Briefly, the clones harbouring the pJW168 plasmid were cultivated at 37° C. or 42° C. on LB and then tested for loss of antibiotic resistance at 30° C. Antibiotic sensitive clones were then verified by PCR using adequate primers.

Example 1: Suppression of the Overexpression of ycdW Gene in an *E. coli* Glycolic Acid Overproducer Recombinant Strain—Description of Strain 1 and Construction of Strains 2 to 3

Description of Strain 1

The strain described in Example 2, part 2 of patent application WO 2011/157728, and which corresponds to the parental strain of AG1413, i.e. the AG1413 strain without the pME101-ycdW-TT07-PaceA-aceA-TT01 plasmid, will be named strain 1 in the current patent application.

Construction of Strain 2

Before using strain 1, the antibiotic resistance cassettes were removed from loci icd (SEQ ID No 01, coding the protein having the sequence of SEQ ID No 02) and aceK (SEQ ID No 03, coding the protein having the sequence of SEQ ID No 04), using the Flp recombinase (according to Protocol 1) and the Cre recombinase (according to Protocol 3), respectively. The kanamycin and chloramphenicol sensible transformants were then selected and the absence of the antibiotic markers was verified by PCR analysis with appropriate oligonucleotides. The strain retained was named strain 2.

Construction of Strain 3

The ycdW gene (SEQ ID No 05, coding the protein having the sequence of SEQ ID No 06), coding for the glyoxylate/hydroxypyruvate reductase, and carried by the pME101-ycdW-TT07-PaceA-aceA-TT01 plasmid described in patent application WO 2010/108909, was removed from this plasmid, together with its promoter and lacI gene (SEQ ID No 07, coding the protein having the sequence of SEQ ID No 08), by restriction enzymes and ligase, giving the pAG0094 plasmid.

The plasmid pAG0094 was introduced into strain 2, giving rise to strain 3.

Example 2: Improving Glyoxylic Acid Production by a Complete Removal of ycdW Gene in an *E. coli* Glycolic Acid Overproducer Recombinant Strain—Construction of Strains 4 to 6

The endogenous copy of ycdW gene was deleted in *E. coli* recombinant glycolic acid producer strain 2.

To achieve the deletion of ycdW gene, the homologous recombination strategy described by Datsenko & Wanner, 2000 (according to Protocol 1) was used.

For ycdW deletion, a fragment carrying a resistance marker flanked by DNA sequences homologous to upstream and downstream regions of the ycdW gene was PCR amplified by the overlapping PCR technique (overlapping oligonucleotides). The sequences for recombination into upstream and downstream regions of ycdW gene are referred to as SEQ ID No 09 and 10. The PCR product obtained "ΔycdW::Km" was then introduced by electroporation into the strain MG1655 (pKD46). The antibiotic resistant transformants were selected and the deletion of ycdW gene with the associated resistance cassette was verified by a PCR analysis with appropriate oligonucleotides. The strain retained was designated MG1655 ΔycdW::Km. Finally, the ΔycdW::Km deletion was transferred by P1 phage transduction (according to Protocol 2) from MG1655 ΔycdW::Km into strain 2. Kanamycin resistant transductants were selected and the presence of LycdW::Km deletion was verified by a PCR analysis with appropriate oligonucleotides. The strain retained was named strain 4.

The endogenous copy of aceA gene (SEQ ID No 11, coding the protein having the sequence of SEQ ID No 12) was then deleted in strain 4.

To achieve the deletion of aceA gene, the homologous recombination strategy described by Datsenko & Wanner, 2000 (according to Protocol 1) was used. As aceB (SEQ ID No 13, coding the protein having the sequence of SEQ ID No 14) and aceK (SEQ ID No 03, coding the protein having the sequence of SEQ ID No 04) genes have been previously deleted in strain 4, the homologous recombination strategy is equivalent to the one used to delete aceBAK operon.

For aceBAK deletion, a fragment carrying an antibiotic resistance marker flanked by DNA sequences homologous to upstream and downstream regions of the aceBAK operon was PCR amplified by the overlapping PCR technique (overlapping oligonucleotides). The sequences for recombination into upstream and downstream regions of aceBAK operon are referred as SEQ ID No 15 and 16. The PCR product obtained "ΔaceBAK::Cm" was then introduced by electroporation into the strain MG1655 (pKD46). The antibiotic resistant transformants were selected and the deletion of aceBAK operon with the associated resistance cassette was verified by a PCR analysis with appropriate oligonucleotides. The strain retained was designated MG1655 ΔaceBAK::Cm. Finally, the ΔaceBAK::Cm deletion was transferred by P1 phage transduction (according to Protocol 2) from MG1655 ΔaceBAK::Cm into strain 4. Chloramphenicol resistant transductants were selected and the presence of ΔaceBAK::Cm deletion was verified by a PCR analysis with appropriate oligonucleotides. The strain retained was named strain 5.

The ycdW gene (SEQ ID No 05 and No 06), coding for the glyoxylate/hydroxypyruvate reductase, and carried by the pME101-ycdW-TT07-PaceA-aceA-TT01 plasmid, was removed from this plasmid by restriction enzymes and ligase, without deleting its promoter and the lacI gene (unlike pAG0094 described in Example 1), giving the pAG0303 plasmid. Therefore, on this plasmid, a part of aceA gene expression is driven via its natural promoter, but it is also possible to increase the level of aceA expression by adding IPTG via the remaining promoter of the ycdW and lacI genes.

The plasmid pAG0303 was introduced into strain 5, giving rise to strain 6.

Example 3: Glycolic Acid and Glyoxylic Acid Production by Fermentation with Strains 3 and 6

Production strains were evaluated in Erlenmeyer baffled flasks.

A 5 mL preculture was grown at 37° C. for 16 hours in a mixed medium (10% LB medium (Sigma 25%) with 2.5 g·L$^{-1}$ glucose and 90% minimal medium M1). It was used to inoculate a 50 mL culture to an OD$_{600}$ of 0.2 in medium M1. The composition of medium M1 is described in Table 1.

When necessary, antibiotics were added in the medium (spectinomycin at a final concentration of 50 mg·L$^{-1}$) and IPTG at a final concentration of 100 µM. The temperature of the cultures was 30° C.

When the culture had reached an $OD_{600}$ up to 5, extracellular metabolites were analysed using HPLC with refractometric detection (organic acids and glucose).

For each strain, several repetitions were performed.

TABLE 1

Composition of M1 medium.

| Compound | Concentration (g · L$^{-1}$) |
|---|---|
| Citric acid•H$_2$O | 6.00 |
| MgSO$_4$•7H$_2$O | 1.00 |
| CaCl$_2$•2H$_2$O | 0.04 |
| CoCl$_2$•6H$_2$O | 0.0080 |
| MnSO$_4$•H$_2$O | 0.0200 |
| CuCl$_2$•2H$_2$O | 0.0020 |
| H$_3$BO$_3$ | 0.0010 |
| Na$_2$MoO$_4$•2H$_2$O | 0.0004 |
| ZnSO$_4$•7H$_2$O | 0.0040 |
| Na$_2$HPO$_4$ | 2.00 |
| KH$_2$PO$_4$ | 10.48 |
| K$_2$HPO$_4$•3H$_2$O | 10.48 |
| (NH$_4$)$_2$HPO$_4$ | 8.00 |
| (NH$_4$)$_2$SO$_4$ | 5.00 |
| NH$_4$Cl | 0.13 |
| FeSO$_4$•7H$_2$O | 0.04 |
| Thiamin | 0.0100 |
| MOPS | 40 |
| Glucose | 10 |

TABLE 2

Glycolic Acid (GA) and Glyoxylic Acid (GxA) titers and yields (Y) in g of GA or GxA per gram of sugar consumed for the producing strains in shake flasks. For the precise definition of GA or GxA/glucose yields see below.

|  | Strain 3 | Strain 6 |
|---|---|---|
| [GA] (g · L$^{-1}$) | 1.1 | 0.4 |
| [GxA] (g · L$^{-1}$) | 0.2 | 0.8 |
| Y GA (g · g$^{-1}$) | 0.11 | 0.03 |
| Y GxA (g · g$^{-1}$) | 0.02 | 0.10 |

As can be seen in Table 2 above, upon the deletion of ycdW copies and the controlled induction of the aceA gene, strain 6 produced much higher amounts of Glyoxylic Acid than strain 3. As expected, this production of glyoxylic acid is linked to the drop of Glycolic Acid synthesis in strain 6.

The GA and GxA yields were expressed as follows:

$$Y_{GA} = \frac{GA\ (g)}{consumed\ glucose\ (g)}$$

$$Y_{GxA} = \frac{GxA\ (g)}{consumed\ glucose\ (g)}$$

Example 4: Improving Glycolic Acid Production by Overexpression of Heterologous Gene Coding for Phosphoketolase Enzyme in an E. coli Glycolic Acid Overproducer Recombinant Strain—Construction of Strains 7 to 12

Construction of Strains 7 to 9: Reconstruction of E. coli Pta Gene Coding for Phosphate Acetyltransferase in an E. coli Glycolic Acid Overproducer Recombinant Strain In strain AG1413 and its parental strain, strain 1, both ackA (SEQ ID No 17, coding the protein having the sequence of SEQ ID No 18) and pta (SEQ ID No 19, coding the protein having the sequence of SEQ ID No 20) genes, which are organized in operons, have been previously deleted. In order to again convert acetyl-phosphate (which is generated by phosphoketolase in the following strains) into acetyl-CoA, the pta gene has been reconstructed into a strain 1 background, while at the same time conserving the deletion of ackA gene.

To achieve the reconstruction of the pta gene, the ΔackA::Km mutant from the Keio collection, deleted only for the ackA gene and carrying a wildtype pta gene, was used. The ΔockA::Km deletion associated with the pta wildtype gene was transferred by P1 phage transduction (according to Protocol 2) from the ΔackA::Km Keio mutant to strain 2. Kanamycin resistant transductants were selected and the presence of both the ΔackA::Km deletion and pta wildtype gene were verified by a PCR analysis with appropriate oligonucleotides. The strain retained was named strain 7.

Then the antibiotic cassette was removed from the ΔackA deletion using the Flp recombinase (according to Protocol 1) in strain 7. The kanamycin sensible transformants were selected and the absence of the antibiotic marker was verified by PCR analysis with appropriate oligonucleotides. The strain retained was named strain 8.

For the Phosphate acetyltransferase activity assay, the phosphate-dependent release of CoA from acetyl-CoA was monitored with Ellman's thiol reagent, 5,5'-dithiobis(2-nitrobenzoic acid) (DTNB), by measuring at 30° C. the formation of the thiophenolate anion at 412 nm ($\varepsilon_{412}$=13.6 mM$^{-1}$ cm$^{-1}$). The assay mixture (1 ml) contained 100 mM KH$_2$PO$_4$ (pH 8), 0.5 mM DTNB, and 1 mM acetyl-CoA. The activity value determined without acetyl-CoA in the assay was subtracted. Specific activity is expressed as milli units (mUI) per milligram of protein.

The phosphate acetyltransferase activity of the strain 7 is 10 times higher than that of strain 8 (1100 mUI/mg for strain 7 and 110 mUI/mg for strain 8).

Then the plasmid pME101-ycdW-TT07-PaceA-aceA-TT01, described in patent application WO2010/108909, was introduced into strain 8, giving rise to strain 9.

Construction of Strains 10 to 12: Overexpression of Heterologous Genes Coding for Phosphoketolase Enzyme in an E. coli Glycolic Acid Overproducer Recombinant Strain In order to increase the acetyl-CoA pool, and thereby glycolic acid production, different phosphoketolases were overproduced in an E. coli glycolic acid overproducer strain.

Three different genes coding for phosphoketolase enzymes were overexpressed individually in strain 9:
- xfp (SEQ ID No 21, coding the protein having the sequence of SEQ ID No 22) from Bifidobacterium animalis,
- fxpk (SEQ ID No 23 coding the protein having the sequence of SEQ ID No 24) from Bifidobacterium adolescentis,
- xpk (SEQ ID No 25 coding the protein having the sequence of SEQ ID No 26) from Lactobacillus pentosus.

For each gene (identified by the "O1ec" suffix), a codon-harmonized version optimized for production in E. coli was synthetically synthesised by GeneArt Gene Synthesis Service from Thermo Fisher Scientific. Each gene was subcloned on a pBBR1MCS5 vector (Kovach et al, 1995), together with the artificial Ptrc promoter (the artificial promoter is the one described for the overexpression of cysPU-WAM operon in patent application WO 2009/043803; Brosius et al, 1985), using the appropriate oligonucleotides, giving respectively the plasmids detailed in Table 3, below.

TABLE 3

Plasmids for the overexpression of phosphoketolase genes

| Origin organism | Name of codon-harmonized version of gene coding for the phosphoketolase | SEQ ID No | Name of plasmids for overexpression of phosphoketolase genes |
|---|---|---|---|
| Bifidobacterium animalis | xfpO1ec | 27 | pBBR1MCS5-Ptrc01-xfpO1ec |
| Bifidobacterium adolescentis | fxpkO1ec | 28 | pBBR1MCS5-Ptrc01-fxpkO1ec |
| Lactobacillus pentosus | xpkO1ec | 29 | pBBR1MCS5-Ptrc01-xpkO1ec |

Each plasmid was individually introduced into strain 9, giving rise to the strains described in Table 4, below.

TABLE 4

Strains comprising plasmids for the overexpression of phosphoketolase genes:

| Name of plasmids for overexpression of phosphoketolase genes | Name of resulting strains corresponding to strain 9 carrying the plasmids |
|---|---|
| pBBR1MCS5-Ptrc01-xfpO1ec | Strain 10 |
| pBBR1MCS5-Ptrc01-fxpkO1ec | Strain 11 |
| pBBR1MCS5-Ptrc01-xpkO1ec | Strain 12 |

The pBBR1 plasmid stably replicates at moderate copy number.

In order to have several levels of overexpression of phosphoketolase genes, the genes were also cloned into the following plasmids with a known different number of copies into the cell:
- the low copy number pCL1920 vector (Lerner & Inouye, 1990) pME101-ycdW-TT07-PaceA-aceA-TT01 plasmid,
- and the one copy number bacterial artificial chromosome pBAC plasmid (Epicentre®).

Phosphoketolase overexpression plasmids, together with pME101-ycdW-TT07-PaceA-aceA-TT01 plasmid, were also introduced in strain 7 and 8.

Performances in Shake Flasks and Reactors

First, strains were evaluated in shake flasks as described in Example 3.

TABLE 5

Glycolic Acid (GA) yields in g of GA per gram of sugar consumed for the producing strains in shake flasks. For the precise definition of GA/glucose yields see Example 3.

| | GA Yield (g · g$^{-1}$) |
|---|---|
| Strain 9 | 0.286 |
| Strain 10 | 0.395 |
| Strain 11 | 0.337 |
| Strain 12 | 0.389 |

As shown in Table 5, upon overexpression of all the tested phosphoketolase genes, the Glycolic Acid production yield increased. The yield was higher with the overexpression of the phosphoketolase genes from *Bifidobacterium animalis* and from *Lactobacillus pentosus*.

These strains were evaluated in 2 L fermenters (Pierre Guerin) using a fedbatch strategy.

A first preculture in tubes was carried out at 37° C. for 10 hours in a mixed medium (10% LB medium (Sigma 25%) with 2.5 g·L$^{-1}$ glucose and 90% minimal medium M1). It was used to inoculate a 50 mL second seed to an OD$_{600}$ of 0.2 in medium M1. This step of preculture was carried out at 37° C. in 500 mL Erlenmeyer flask filled with 50 mL of synthetic medium (M1) supplemented with 40 g·L$^{-1}$ of MOPS and 10 g·L$^{-1}$ of glucose. This second preculture was used for the inoculation of the fermentor after getting an OD$_{600\ nm}$ close to 9.

The reactor filled with 700 mL of synthetic medium (M2) supplemented with 20 g·L$^{-1}$ of glucose, was inoculated at an initial optical density of about 0.5. The composition of M2 medium is described in Table 6. The culture was carried out at 30° C. with agitation and the dissolved oxygen concentration was maintained at values between 20 and 40%, preferentially 30% saturation, by increasing the agitation and aeration. The pH was adjusted to 6.8 by automatic addition of NH$_4$OH/NaOH solution (15/5 w/w).

The culture was conducted in a batch mode until exhaustion of glucose. At that time, a solution of 700 g·L$^{-1}$ glucose supplemented with magnesium sulfate, oligo-elements and thiamine was added to restore a concentration of 20 g·L$^{-1}$ of glucose in the reactor. Further additions were performed each time that glucose was once again exhausted. After the fifth pulse, the pH was increased to the value of 7.4 thanks to a ramp of three hours.

The cultures were stopped after 40 to 45 hours. Extracellular metabolites were analysed using HPLC with refractometric detection (organic acids and glucose).

For each strain, several repetitions were performed. The final performances are presented in Table 7.

TABLE 6

Composition of M2 medium.

| Compound | Concentration (g · L$^{-1}$) |
|---|---|
| Citric acid•H$_2$O | 3.00 |
| MgSO$_4$•7H$_2$O | 1.00 |
| CaCl$_2$•2H$_2$O | 0.04 |
| CoCl$_2$•6H$_2$O | 0.0080 |
| MnSO$_4$•H$_2$O | 0.0200 |
| CuCl$_2$•2H$_2$O | 0.0020 |
| H$_3$BO$_3$ | 0.0010 |
| Na$_2$MoO$_4$•2H$_2$O | 0.0004 |
| ZnSO$_4$•7H$_2$O | 0.0040 |
| KH$_2$PO$_4$ | 0.70 |
| K$_2$HPO$_4$•3H$_2$O | 1.17 |
| NH$_4$H$_2$PO$_4$ | 2.99 |
| (NH$_4$)$_2$HPO$_4$ | 3.45 |
| (NH$_4$)$_2$SO$_4$ | 8.75 |
| NH$_4$Cl | 0.13 |
| FeSO$_4$•7H$_2$O | 0.04 |
| Thiamin | 0.0100 |

TABLE 7

Final performances of strains 9, 10 and 12 in 2 L reactors.

| Strain | GA final Titer | GA final productivity | GA final Yield |
|---|---|---|---|
| Strain 9 | Reference | Reference | Reference |
| Strain 10 | ~ | ~ | ++ |
| Strain 12 | ~ | ~ | + |

The symbol ~ indicates that the variation of the parameter is between −5% and 5% compared to the reference strain. The symbol + indicates an increase between 5 and 10% and the symbol ++ indicates an increase between 10 and 20%.

Upon overexpression of phosphoketolase genes, the production yield of strains 10 and 12 shows an increase between 5 to 20% according to the nature of the heterologous gene tested. We did not see any effect on the titer or on the productivity. With these results, the benefit of the phosphoketolase activity on GA production was confirmed.

Levels of expression of the phosphoketolase genes did not change the tendency of the results. Glycolic acid production was improved with different levels of overexpression of the 3 genes; xfpO1ec, fxpkO1ec, xpkO1e, carried on pCL1920 or on pBAC (data not shown).

Yields are Calculated as Follows:

The fermentor volume was calculated by adding to the initial volume the amount of solutions added to regulate the pH and to feed the culture and by subtracting the volume used for sampling and lost by evaporation.

The fedbatch volume was followed continuously by weighing the feeding stock. The amount of injected glucose was then calculated on the basis of the injected weight, the density of the solution and the glucose concentration controlled by the method of Brix ([Glucose]). The GA yield was expressed as follows:

$$Y_{GA} = \frac{GA_f * V_f - GA_0 * V_0}{\text{Consumed glucose}}$$

$GA_0$ and $GA_f$ correspond respectively to the initial and final GA concentrations, and $V_0$ and $V_f$ to the initial and the final volumes. The consumed glucose is expressed in g.

D-Xylulose 5-Phosphate and Fructose 6-Phosphate Phosphoketolase Assays on Crude Extract (X5PPK and F6PPK)

Phosphoketolase activity was measured spectrophotometrically as ferric acetyl hydroxamate produced from the enzymatically generated acetyl phosphate according to Racker et al, 1962 and Meile et al, 2001. The standard reaction mixture of 0.075 ml consisted of 33.3 mM potassium phosphate (pH 6.5), L-cysteine hydrochloride (1.9 mM), sodium fluoride (23 mM), sodium iodoacetate (8 mM), either D-fructose 6-phosphate (F6P) (100 mM) or D-xylulose 5-phosphate (X5P) (27 mM) as a substrate and the crude extract to initiate the reaction. After incubating at 37° C. for 10 or 30 min, the enzymatic reaction was stopped by the addition of 0.075 ml of hydroxylamine hydrochloride (2 M, pH 6.5). After ten minutes at room temperature, 0.05 ml of 15% (wt/vol) trichloroacetic acid, 0.05 ml of 4 M HCl, and 0.05 ml of $FeCl_3 \times 6\, H_2O$ (5% [wt/vol] in 0.1 M HCl) were added for the final color development of the ferric hydroxamate. After incubation at 25° C. under agitation for 5 min, the mix was centrifuged for 5 min at 2250×g, 200 µl of supernatant was transferred to a new micro plate to measure the absorbance. The formation of ferric hydroxamate was then spectrophotometrically quantified at 505 nm by comparing to a series of acetyl phosphate standards between 1.5 mM and 150 mM. One unit of phosphoketolase activity is defined as the amount of extract forming 1 mmol of acetyl phosphate per min from either F6P or X5P. The activity value determined without substrate in the assay was subtracted. Specific activity is expressed as milli units per milligram of protein.

The D-Xylulose 5-Phosphate and Fructose 6-Phosphate phosphoketolase activities of strains 10 to 12 are provided in Table 8.

TABLE 8

D-Xylulose 5-Phosphate and 6-Phosphate phosphoketolase activities measured on crude extract

| Strain | X5PPK activity mUI/mg | F6PPK activity mUI/mg |
|---|---|---|
| Strain 9 | ND | ND |
| Strain 10 | 690 | 250 |
| Strain 11 | 115 | 30 |
| Strain 12 | 650 | ND |

ND: Not detectable

The phosphoketolase enzymes encoded by xfp from *Bifidobacterium animalis* and fxpk from *Bifidobacterium adolescentis* expressed in *E. coli* catalyse both activities on Xylulose 5-phosphate and fructose 6-phopshate substrates. Nevertheless, these enzymes are more active on the substrate Xylulose 5-phosphate than on the fructose 6-phopshate as can be seen in Table 8. In contrast, the phosphoketolase enzyme encoded by xpk from *Lactobacillus pentosus* expressed in *E. coli* was exclusively active on the substrate Xylulose 5-phosphate.

Results of this example, showing Glycolic Acid production of strains 10, 11 and 12 that carry different phosphoketolase (PK) enzymes as compared to a referent strain 9 without any PK, demonstrate that the phosphoketolase activity improves the yield of Glycolic Acid per glucose consumed regardless of the substrate specificity of the enzyme (X5PPK or F6PPK).

Example 5: Improving Glyoxylic Acid Production by Both Suppression of ycdW Expression and Overexpression of Heterologous Genes Coding for Phosphoketolase Enzyme in an *E. coli* Glycolic Acid Overproducer Recombinant Strain—Construction of Strains 13 to 17

Construction of Strains 13 and 14: Suppression of Expression of *E. coli* ycdW Gene Coding for Glyoxylate/Hydroxypyruvate Reductase in ΔackA+pta AG1413 Strain The strain AG1413 possesses two copies of the ycdW gene, one on the chromosome and one on the pME101-ycdW-TT07-PaceA-aceA-TT01 plasmid.

To delete the chromosomal copy of ycdW in a strain AG1413 background, the ΔycdW::Km deletion, described in Example 2, was transferred by P1 phage transduction (according to Protocol 2) from MG1655 ΔycdW::Km into strain 2. Kanamycin resistant transductants were selected and the presence of ΔycdW::Km deletion was verified by a PCR analysis with appropriate oligonucleotides. The strain retained was named strain 13.

Then, the plasmid pAG0303 described in Example 2, overexpressing aceA gene without the ycdW gene, was introduced into strain 13, giving rise to strain 14.

Construction of Strains 15 to 16: Suppression of Expression of the *E. coli* ycdW Gene Coding for Glyoxylate/Hydroxypyruvate Reductase in Pta Wild-Type Strain 9

The strain 9 possesses two copies of the ycdW gene, one on the chromosome and one on the pME101-ycdW-TT07-PaceA-aceA-TT01 plasmid.

To delete the chromosomal copy of ycdW in a strain 9 background, the ΔycdW::Km deletion, described in Example 2, was transferred by P1 phage transduction (according to Protocol 2) from MG1655 ΔycdW::Km into strain 8. Kanamycin resistant transductants were selected and the presence of ΔycdW::Km deletion was verified by a PCR analysis with appropriate oligonucleotides. The strain retained was named strain 15.

Then the plasmid pAG0303 described in Example 2, overexpressing aceA gene without the ycdW gene, was introduced into strain 15, giving rise to strain 16.

Construction of Strain 17: Overexpression of *Bifidobacterium animalis* Gene Coding for Phosphoketolase Enzyme in an *E. coli* Glyoxylic Acid Overproducer Recombinant Strain The codon-harmonized version of *Bifidobacterium animalis* xfpO1ec gene coding for phosphoketolase enzyme was overexpressed into strain 16.

To overexpress this gene into strain 16, the plasmid pBBR1MCS5-Ptrc01-xfpO1ec described in Example 4, was introduced into strain 16, giving rise to strain 17.

In order to test different levels of overexpression of the phosphoketolase gene, the xfpO1ec gene was also cloned into a plasmid with a smaller copy number than pBBR1: the low copy number pCL1920 vector (Lerner & Inouye, 1990), pAG303 described in Example 2.

All modifications described above were also made in a strain 7 background.

The same work was also performed for both of the other phosphoketolase genes, fxpkO1ec and xpkO1ec.

Performances in Shake Flasks

Strains were evaluated in shake flasks as described in Example 3.

TABLE 9

Glyoxylic Acid (GxA) yields in g of GxA per gram of sugar consumed for the producing strains in shake flasks. For the precise definition of GxA/glucose yields see Example 3.

| Strain | GxA Yield (g · g⁻¹) |
|---|---|
| Strain 14 | 0.02 |
| Strain 16 | 0.02 |
| Strain 17 | 0.03 |

As can be seen in Table 9 above, the overexpression of phosphoketolase gene from *Bifidobacterium animalis* slightly increased the production of Glyoxylic Acid (strain 17 versus strain 14).

The same results, an increase in glyoxylic acid production, were also obtained with the other phosphoketolase enzymes tested (data not shown).

D-Xylulose 5-Phosphate and Fructose 6-Phosphate Phosphoketolase Assays on Crude Extract (X5PPK and F6PPK)

Phosphoketolase activity was measured according to the protocol described above in Example 4. The D-Xylulose 5-Phosphate and Fructose 6-Phosphate phosphoketolase activities of strains 16 and 17 are provided in Table 10.

TABLE 10

D-Xylulose 5-Phosphate and 6-Phosphate phosphoketolase activities measured on crude extract

| Strain | X5PPK activity mUI/mg | F6PPK activity mUI/mg |
|---|---|---|
| Strain 16 | ND | ND |
| Strain 17 | 710 | 300 |

ND: Not detectable

The phosphoketolase enzyme encoded by xfp from *Bifidobacterium animalis* and expressed in *E. coli* catalyses both activities on Xylulose 5-phosphate and fructose 6-phopshate substrates. The enzyme was more active on the substrate Xylulose 5-phosphate.

BIBLIOGRAPHIC REFERENCES

Brosius J, Erfle M, Storella J, (1985), J Biol Chem., 260(6): 3539-41
Datsenko K A & Wanner B L, (2000), Proc Natl Acad Sci USA., 97: 6640-6645
Cativiela C, Fraile J M, Garcia J I, Lazaro B, Mayoral J A, Pallares A, (2003), Green Chemistry, 5: 275-277
Furukawa K, Inada H, Shibuya M, Yamamoto Y, (2016), Org. Lett., 18(17): 4230-4233
Isobe K & Nishise H, (1999), J. Biotechnol., 75: 265-271
Job V, Marcone G L, Pilone M S, Pollegioni L, (2002), J. Biol. Chem., 277(9): 6985-6993
Kataoka M, Sasaki M, Hidalgo A R, Nakano M, Shimizu S, (2001), Biosci. Biotechnol. Biochem, 65(10): 2265-2270
Kovach M E, Elzer P H, Hill D S, Robertson G T, Farris M A, Roop R M 2nd, Peterson K M, (1995), Gene., 166(1): 175-6
Lerner C G, Inouye M, (1990), Nucleic Acids Res., 18(15): 4631
Loewen & Switala, (1986), Biochem Cell Biol., 64(7):638-46.
Meile L, Rohr L M, Geissmann T A, Herensperger M, Teuber M, (2001), J Bacteriol., 183 (9), 2929-2936
Nishiya Y & Imanaka T, (1998), FEBS Letters, 438: 263-266
Palmeros B, Wild I, Szybalski W, Le Borgne S, Hernandez-Chavez G, Gosset G, Valle F, Bolivar F., (2000), Gene, 247(1-2): 255-64
Papini M, Nookaew I, Siewer V, Nielsen J, (2012), Appl. Microbiol. Biotechnol., 95: 1001-1010
Posthuma C C, Bader R, Engelmann R, Postma P W, Hengstenberg W, Pouwels P H, (2002), Appl. Environ. Microbiol., 68(9): 831-837
Racker E, (1962), Methods Enzymol., 5, 276-280
Sardari R R R, Dishisha T, Pyo S H, Hatti-Kaul R, (2014), J. Biotechnol., 192: 223-230

The invention claimed is:

1. A method for the production of glycolic acid and/or glyoxylic acid from carbohydrate as a sole carbon source using at least one step of fermentation and a modified microorganism wherein in said modified microorganism:
Expression of at least one gene selected from the group consisting of aceB, glcB, gcl and eda is attenuated and,
Expression of at least one gene encoding xylulose 5-Phosphate phosphoketolase and/or fructose 6-Phosphate phosphoketolase is enhanced.

2. The method according to claim 1, wherein the gene encoding the phosphoketolase is selected from the group consisting of: xpkA gene from *Lactobacillus pentosus*, xfp gene from *Bifidobacterium animalis*, xfp gene from *Bifidobacterium lactis*, and their homologous genes.

3. The method for the production of glycolic acid according to claim 1, wherein the modified microorganism further overexpresses ycdW gene from *Escherichia coli* or at least one of its homologous genes.

4. The method according to claim 3 for the production of glyoxylic acid from glycolic acid further comprising the steps of:
Converting glycolic acid into glyoxylic acid either by bioconversion from glycolic acid using a glycolate oxidase encoded by gldDEFG genes from *Escherichia coli* and a catalase encoded by the gene katE or katG from *Escherichia coli*, or by chemical conversion using a nitroxyl radical catalyst,
Recovering glyoxylic acid.

5. The method of claim 4, wherein glycolate oxidase and catalase are expressed in the same microorganism.

6. The method for the production of glyoxylic acid according to claim 1, wherein in the modified microorganism, at least ycdW gene from *Escherichia coli* is attenuated.

7. The method according to claim 6 for the production of glycolic acid from glyoxylic acid further comprising the steps of:
Converting glyoxylic acid into glycolic acid either by bioconversion from glyoxylic acid using a glyoxylate reductase encoded by the gene ycdW from *Escherichia coli* or by the gene grxA from *Rhizobium etli*, or by chemical conversion using sodium borohydride,
Recovering glycolic acid.

8. The method of claim 1, wherein glycolic acid is purified by steps of crystallization, distillation, liquid-liquid extraction or extractive fermentation.

9. The method of claim 1, wherein glyoxylic acid is purified by steps of ion exchange, crystallization, precipitation or extractive fermentation.

10. A microorganism modified for the production of glycolic acid or glyoxylic acid wherein:
Expression of at least one gene selected from the group consisting of aceB, glcB, gcl and eda is attenuated, and
Expression of at least one gene encoding phosphoketolase is enhanced.

11. The microorganism of claim 10, wherein the gene encoding the phosphoketolase is selected from the group consisting of: xpkA gene from *Lactobacillus pentosus*, xfp gene from *Bifidobacterium animalis*, xfp gene from *Bifidobacterium lactis*, and their homologous genes.

12. The microorganism of claim 10, further comprising:
overexpression of ycdW gene from *Escherichia coli* or at least one of its homologous genes for the production of glycolic acid, or
attenuation of the expression of at least ycdW gene from *Escherichia coli* for the production of glyoxylic acid.

13. The microorganism of claim 10, wherein the microorganism is selected from the group consisting of Enterobacteriaceae, Clostridiaceae, Corynebacteriaceae, Bacillaceae, Bifidobacteriaceae, Lactobacillaceae, and yeast.

14. The microorganism according to claim 13, wherein said microorganism is from the *Escherichia coli* species.

15. The method of claim 4, further comprising a step of isolating glycolic acid from fermentation broth prior to the step of converting glycolic acid into glyoxylic acid.

16. The method of claim 7, further comprising a step of isolating glycolic acid from fermentation broth prior to the step of converting glyoxylic acid into glycolic acid.

* * * * *

SEQUENCE LISTING

<160> NUMBER OF SEQ ID NOS: 29

<210> SEQ ID NO 1
<211> LENGTH: 1251
<212> TYPE: DNA
<213> ORGANISM: Escherichia coli

<400> SEQUENCE: 1
atggaaagta aagtagttgt tccggcacaa ggcaagaaga tcaccctgca aaacggcaaa    60

```
ctcaacgttc ctgaaaatcc gattatccct tacattgaag gtgatggaat cggtgtagat      120
gtaaccccag ccatgctgaa agtggtcgac gctgcagtcg agaaagccta taaaggcgag      180
cgtaaaatct cctggatgga aatttacacc ggtgaaaaat ccacacaggt ttatggtcag      240
gacgtctggc tgcctgctga aactcttgat ctgattcgtg aatatcgcgt tgccattaaa      300
ggtccgctga ccactccggt tggtggcggt attcgctctc tgaacgttgc cctgcgccag      360
gaactggatc tctacatctg cctgcgtccg gtacgttact atcagggcac tccaagcccg      420
gttaaacacc ctgaactgac cgatatggtt atcttccgtg aaaactcgga agacatttat      480
gcgggtatcg aatggaaagc agactctgcc gacgccgaga agtgattaa attcctgcgt      540 gaagagatgg gggtgaagaa aattcgcttc ccggaacatt gtggtatcgg tattaagccg      600
tgttcggaag aaggcaccaa acgtctggtt cgtgcagcga tcgaatacgc aattgctaac      660
gatcgtgact ctgtgactct ggtgcacaaa gcaacatca tgaagttcac cgaaggagcg      720
tttaaagact ggggctacca gctggcgcgt gaagagtttg gcggtgaact gatcgacggt      780
ggcccgtggc tgaaagttaa aaacccgaac actggcaaag atcgtcat taagacgtg       840 attgctgatg cattcctgca acagatcctg ctgcgtccgg ctgaatatga tgttatcgcc      900
tgtatgaacc tgaacggtga ctacatttct gacgccctgg cagcgcaggt tggcggtatc      960
ggtatcgccc tggtgcaaa catcggtgac gaatgcgccc tgtttgaagc cacccacggt     1020
actgcgccga aatatgccgg tcaggacaaa gtaaatcctg gctctattat tctctccgct     1080
gagatgatgc tgcgccacat gggttggacc gaagcggctg acttaattgt taaaggtatg     1140
gaaggcgcaa tcaacgcgaa aaccgtaacc tatgacttcg agcgtctgat ggatggcgct     1200
aaactgctga atgttcaga gtttggtgac gcgatcatcg aaaacatgta a             1251
```

<210> SEQ ID NO 2
<211> LENGTH: 416
<212> TYPE: PRT
<213> ORGANISM: Escherichia coli

<400> SEQUENCE: 2

Met Glu Ser Lys Val Val Pro Ala Gln Gly Lys Lys Ile Thr Leu
1               5                   10                  15

Gln Asn Gly Lys Leu Asn Val Pro Glu Asn Pro Ile Ile Pro Tyr Ile
                20                  25                  30

Glu Gly Asp Gly Ile Gly Val Asp Val Thr Pro Ala Met Leu Lys Val
            35                  40                  45

Val Asp Ala Ala Val Glu Lys Ala Tyr Lys Gly Glu Arg Lys Ile Ser
        50                  55                  60

Trp Met Glu Ile Tyr Thr Gly Glu Lys Ser Thr Gln Val Tyr Gly Gln
65                  70                  75                  80

Asp Val Trp Leu Pro Ala Glu Thr Leu Asp Leu Ile Arg Glu Tyr Arg
                85                  90                  95

Val Ala Ile Lys Gly Pro Leu Thr Thr Pro Val Gly Gly Gly Ile Arg
            100                 105                 110

Ser Leu Asn Val Ala Leu Arg Gln Glu Leu Asp Leu Tyr Ile Cys Leu
        115                 120                 125

Arg Pro Val Arg Tyr Tyr Gln Gly Thr Pro Ser Pro Val Lys His Pro
    130                 135                 140

Glu Leu Thr Asp Met Val Ile Phe Arg Glu Asn Ser Glu Asp Ile Tyr
145                 150                 155                 160

Ala Gly Ile Glu Trp Lys Ala Asp Ser Ala Asp Ala Glu Lys Val Ile
            165                 170                 175

Lys Phe Leu Arg Glu Glu Met Gly Val Lys Lys Ile Arg Phe Pro Glu
        180                 185                 190

His Cys Gly Ile Gly Ile Lys Pro Cys Ser Glu Glu Gly Thr Lys Arg
    195                 200                 205

Leu Val Arg Ala Ala Ile Glu Tyr Ala Ile Ala Asn Asp Arg Asp Ser
210                 215                 220

Val Thr Leu Val His Lys Gly Asn Ile Met Lys Phe Thr Glu Gly Ala
225                 230                 235                 240

Phe Lys Asp Trp Gly Tyr Gln Leu Ala Arg Glu Glu Phe Gly Gly Glu
                245                 250                 255

Leu Ile Asp Gly Gly Pro Trp Leu Lys Val Lys Asn Pro Asn Thr Gly
            260                 265                 270

Lys Glu Ile Val Ile Lys Asp Val Ile Ala Asp Ala Phe Leu Gln Gln
        275                 280                 285

Ile Leu Leu Arg Pro Ala Glu Tyr Asp Val Ile Ala Cys Met Asn Leu
    290                 295                 300

Asn Gly Asp Tyr Ile Ser Asp Ala Leu Ala Ala Gln Val Gly Gly Ile
305                 310                 315                 320

Gly Ile Ala Pro Gly Ala Asn Ile Gly Asp Glu Cys Ala Leu Phe Glu
                325                 330                 335

Ala Thr His Gly Thr Ala Pro Lys Tyr Ala Gly Gln Asp Lys Val Asn
            340                 345                 350

Pro Gly Ser Ile Ile Leu Ser Ala Glu Met Met Leu Arg His Met Gly
        355                 360                 365

Trp Thr Glu Ala Ala Asp Leu Ile Val Lys Gly Met Glu Gly Ala Ile
    370                 375                 380

Asn Ala Lys Thr Val Thr Tyr Asp Phe Glu Arg Leu Met Asp Gly Ala
385                 390                 395                 400

Lys Leu Leu Lys Cys Ser Glu Phe Gly Asp Ala Ile Ile Glu Asn Met
                405                 410                 415

<210> SEQ ID NO 3
<211> LENGTH: 1737
<212> TYPE: DNA
<213> ORGANISM: Escherichia coli

<400> SEQUENCE: 3
atgccgcgtg gcctggaatt attgattgct caaaccattt tgcaaggctt cgatgctcag      60
tatggtcgat tcctcgaagt gacctccggt gcgcagcagc gtttcgaaca ggccgactgg     120
catgctgtcc agcaggcgat gaaaaaccgt atccatcttt acgatcatca cgttggtctg     180
gtcgtggagc aactgcgctg cattactaac ggccaaagta cggacgcggc attttactg      240 cgtgttaaag agcattacac ccggctgttg ccggattacc cgcgcttcga gattgcggag     300 agcttttta actccgtgta ctgtcggtta tttgaccacc gctcgcttac tcccgagcgg     360 cttttatct ttagctctca gccagagcgc cgctttcgta ccattccccg cccgctggcg     420
aaagactttc accccgatca cggctgggaa tctctactga tgcgcgttat cagcgaccta     480
ccgctgcgcc tgcgctggca gaataaaagc cgtgacatcc attacattat cgccatctg      540 acggaaacgc tggggacaga caacctcgcg gaaagtcatt tacaggtggc gaacgaactg     600
ttttaccgca taaagccgc ctggctggta ggcaaactga tcacaccttc ggcacattg       660 ccattttgc tgccgatcca ccagacggac gacggcgagt tatttattga tacctgcctg     720

```
acgacgaccg ccgaagcgag cattgttttt ggctttgcgc gttcttattt tatggtttat    780
gcgccgctgc ccgcagcgct ggtcgagtgg ctacgggaaa ttctgccagg taaaaccacc    840
gctgaattgt atatggctat cggctgccag aagcacgcca aaaccgaaag ctaccgcgaa    900
tatctcgttt atctacaggg ctgtaatgag cagttcattg aagcgccggg tattcgtgga    960
atggtgatgt tggtgtttac gctgccgggc tttgatcggg tattcaaagt catcaaagac   1020
aggttcgcgc gcagaaaga gatgtctgcc gctcacgttc gtgcctgcta tcaactggtg   1080
aaagagcacg atcgcgtggg ccgaatggcg gacacccagg agtttgaaaa ctttgtgctg   1140
gagaagcggc atatttcccc ggcattaatg gaattactgc ttcaggaagc agcggaaaaa   1200
atcaccgatc tcggcgaaca aattgtgatt cgccatcttt atattgagcg gcggatggtg   1260
ccgctcaata tctggctgga acaagtggaa ggtcagcagt gcgcgacgc cattgaagaa   1320 tacggtaacg ctattcgcca gcttgccgct gctaacattt tccctggcga catgctgttt   1380
aaaaacttcg gtgtcacccg tcacgggcgt gtggtttttt atgattacga tgaaatttgc   1440
tacatgacgg aagtgaattt ccgcgacatc ccgccgccgc gctatccgga agacgaactt   1500
gccagcgaac gtggtacag cgtctcgccg ggcgatgttt ccccggaaga gtttcgccac   1560
tggctatgcg ccgacccgcg tattggtccg ctgtttgaag agatgcacgc cgacctgttc   1620
cgcgctgatt actggcgcgc actacaaaac cgcatacgtg aagggcatgt ggaagatgtt   1680
tatgcgtatc ggcgcaggca agatttagc gtacggtatg gggagatgct ttttga       1737

<210> SEQ ID NO 4
<211> LENGTH: 578
<212> TYPE: PRT
<213> ORGANISM: Escherichia coli

<400> SEQUENCE: 4

Met Pro Arg Gly Leu Glu Leu Leu Ile Ala Gln Thr Ile Leu Gln Gly
1               5                   10                  15

Phe Asp Ala Gln Tyr Gly Arg Phe Leu Glu Val Thr Ser Gly Ala Gln
                20                  25                  30

Gln Arg Phe Glu Gln Ala Asp Trp His Ala Val Gln Gln Ala Met Lys
            35                  40                  45

Asn Arg Ile His Leu Tyr Asp His His Val Gly Leu Val Val Glu Gln
        50                  55                  60

Leu Arg Cys Ile Thr Asn Gly Gln Ser Thr Asp Ala Ala Phe Leu Leu
65                  70                  75                  80

Arg Val Lys Glu His Tyr Thr Arg Leu Leu Pro Asp Tyr Pro Arg Phe
                85                  90                  95

Glu Ile Ala Glu Ser Phe Phe Asn Ser Val Tyr Cys Arg Leu Phe Asp
                100                 105                 110

His Arg Ser Leu Thr Pro Glu Arg Leu Phe Ile Phe Ser Ser Gln Pro
            115                 120                 125

Glu Arg Arg Phe Arg Thr Ile Pro Arg Pro Leu Ala Lys Asp Phe His
        130                 135                 140

Pro Asp His Gly Trp Glu Ser Leu Leu Met Arg Val Ile Ser Asp Leu
145                 150                 155                 160

Pro Leu Arg Leu Arg Trp Gln Asn Lys Ser Arg Asp Ile His Tyr Ile
                165                 170                 175

Ile Arg His Leu Thr Glu Thr Leu Gly Thr Asp Asn Leu Ala Glu Ser
                180                 185                 190
```

His Leu Gln Val Ala Asn Glu Leu Phe Tyr Arg Asn Lys Ala Ala Trp
          195                 200                 205

Leu Val Gly Lys Leu Ile Thr Pro Ser Gly Thr Leu Pro Phe Leu Leu
     210                 215                 220

Pro Ile His Gln Thr Asp Asp Gly Glu Leu Phe Ile Asp Thr Cys Leu
225                 230                 235                 240

Thr Thr Thr Ala Glu Ala Ser Ile Val Phe Gly Phe Ala Arg Ser Tyr
                 245                 250                 255

Phe Met Val Tyr Ala Pro Leu Pro Ala Leu Val Glu Trp Leu Arg
             260                 265                 270

Glu Ile Leu Pro Gly Lys Thr Thr Ala Glu Leu Tyr Met Ala Ile Gly
         275                 280                 285

Cys Gln Lys His Ala Lys Thr Glu Ser Tyr Arg Glu Tyr Leu Val Tyr
    290                 295                 300

Leu Gln Gly Cys Asn Glu Gln Phe Ile Glu Ala Pro Gly Ile Arg Gly
305                 310                 315                 320

Met Val Met Leu Val Phe Thr Leu Pro Gly Phe Asp Arg Val Phe Lys
                 325                 330                 335

Val Ile Lys Asp Arg Phe Ala Pro Gln Lys Glu Met Ser Ala Ala His
             340                 345                 350

Val Arg Ala Cys Tyr Gln Leu Val Lys Glu His Asp Arg Val Gly Arg
        355                 360                 365

Met Ala Asp Thr Gln Glu Phe Glu Asn Phe Val Leu Glu Lys Arg His
    370                 375                 380

Ile Ser Pro Ala Leu Met Glu Leu Leu Leu Gln Glu Ala Ala Glu Lys
385                 390                 395                 400

Ile Thr Asp Leu Gly Glu Gln Ile Val Ile Arg His Leu Tyr Ile Glu
                 405                 410                 415

Arg Arg Met Val Pro Leu Asn Ile Trp Leu Glu Gln Val Glu Gly Gln
             420                 425                 430

Gln Leu Arg Asp Ala Ile Glu Glu Tyr Gly Asn Ala Ile Arg Gln Leu
        435                 440                 445

Ala Ala Ala Asn Ile Phe Pro Gly Asp Met Leu Phe Lys Asn Phe Gly
    450                 455                 460

Val Thr Arg His Gly Arg Val Val Phe Tyr Asp Tyr Asp Glu Ile Cys
465                 470                 475                 480

Tyr Met Thr Glu Val Asn Phe Arg Asp Ile Pro Pro Arg Tyr Pro
                 485                 490                 495

Glu Asp Glu Leu Ala Ser Glu Pro Trp Tyr Ser Val Ser Pro Gly Asp
             500                 505                 510

Val Phe Pro Glu Glu Phe Arg His Trp Leu Cys Ala Asp Pro Arg Ile
        515                 520                 525

Gly Pro Leu Phe Glu Glu Met His Ala Asp Leu Phe Arg Ala Asp Tyr
    530                 535                 540

Trp Arg Ala Leu Gln Asn Arg Ile Arg Glu Gly His Val Glu Asp Val
545                 550                 555                 560

Tyr Ala Tyr Arg Arg Arg Gln Arg Phe Ser Val Arg Tyr Gly Glu Met
                 565                 570                 575

Leu Phe

<210> SEQ ID NO 5
<211> LENGTH: 939
<212> TYPE: DNA
<213> ORGANISM: Escherichia coli

<400> SEQUENCE: 5

```
atggatatca tcttttatca cccaacgttc gatacccaat ggtggattga ggcactgcgc      60
aaagctattc ctcaggcaag agtcagagca tggaaaagcg agataatga ctctgctgat     120
tatgctttag tctggcatcc tcctgttgaa atgctggcag gcgcgatct aaagcggtg      180
ttcgcactcg gggccggtgt tgattctatt ttgagcaagc tacaggcaca ccctgaaatg     240
ctgaacccct ctgttccact ttttcgcctg gaagataccg gtatgggcga gcaaatgcag     300
gaatatgctg tcagtcaggt gctgcattgg tttcgacgtt ttgacgatta tcgcatccag     360
caaaatagtt cgcattggca accgctgcct gaatatcatc gggaagattt taccatcggc     420
attttgggcg caggcgtact gggcagtaaa gttgctcaga gtctgcaaac ctggcgcttt     480
ccgctgcgtt gctggagtcg aacccgtaaa tcgtggcctg gcgtgcaaag ctttgccgga     540
cgggaagaac tgtctgcatt tctgagccaa tgtcgggtat tgattaattt gttaccgaat     600
acccctgaaa ccgtcggcat tattaatcaa caattactcg aaaaattacc ggatggcgcg     660
tatctcctca acctggcgcg tggtgttcat gttgtggaag atgacctgct cgcggcgctg     720
gatagcggca agttaaaggc gcaatgttg gatgttttta atcgtgaacc cttaccgcct     780
gaaagtccgc tctggcaaca tccacgcgtg acgataacac cacatgtcgc cgcgattacc     840
cgtcccgctg aagctgtgga gtacatttct cgcaccattg cccagctcga aaaggggag     900
agggtctgcg ggcaagtcga ccgcgcacgc ggctactaa                           939
```

<210> SEQ ID NO 6
<211> LENGTH: 312
<212> TYPE: PRT
<213> ORGANISM: Escherichia coli

<400> SEQUENCE: 6

```
Met Asp Ile Ile Phe Tyr His Pro Thr Phe Asp Thr Gln Trp Trp Ile
1               5                   10                  15

Glu Ala Leu Arg Lys Ala Ile Pro Gln Ala Arg Val Arg Ala Trp Lys
            20                  25                  30

Ser Gly Asp Asn Asp Ser Ala Asp Tyr Ala Leu Val Trp His Pro Pro
        35                  40                  45

Val Glu Met Leu Ala Gly Arg Asp Leu Lys Ala Val Phe Ala Leu Gly
    50                  55                  60

Ala Gly Val Asp Ser Ile Leu Ser Lys Leu Gln Ala His Pro Glu Met
65                  70                  75                  80

Leu Asn Pro Ser Val Pro Leu Phe Arg Leu Glu Asp Thr Gly Met Gly
                85                  90                  95

Glu Gln Met Gln Glu Tyr Ala Val Ser Gln Val Leu His Trp Phe Arg
            100                 105                 110

Arg Phe Asp Asp Tyr Arg Ile Gln Gln Asn Ser Ser His Trp Gln Pro
        115                 120                 125

Leu Pro Glu Tyr His Arg Glu Asp Phe Thr Ile Gly Ile Leu Gly Ala
    130                 135                 140

Gly Val Leu Gly Ser Lys Val Ala Gln Ser Leu Gln Thr Trp Arg Phe
145                 150                 155                 160

Pro Leu Arg Cys Trp Ser Arg Thr Arg Lys Ser Trp Pro Gly Val Gln
                165                 170                 175

Ser Phe Ala Gly Arg Glu Glu Leu Ser Ala Phe Leu Ser Gln Cys Arg
            180                 185                 190
```

Val Leu Ile Asn Leu Leu Pro Asn Thr Pro Glu Thr Val Gly Ile Ile
        195                 200                 205

Asn Gln Gln Leu Leu Glu Lys Leu Pro Asp Gly Ala Tyr Leu Leu Asn
    210                 215                 220

Leu Ala Arg Gly Val His Val Val Glu Asp Asp Leu Leu Ala Ala Leu
225                 230                 235                 240

Asp Ser Gly Lys Val Lys Gly Ala Met Leu Asp Val Phe Asn Arg Glu
                245                 250                 255

Pro Leu Pro Pro Glu Ser Pro Leu Trp Gln His Pro Arg Val Thr Ile
            260                 265                 270

Thr Pro His Val Ala Ala Ile Thr Arg Pro Ala Glu Ala Val Glu Tyr
        275                 280                 285

Ile Ser Arg Thr Ile Ala Gln Leu Glu Lys Gly Glu Arg Val Cys Gly
    290                 295                 300

Gln Val Asp Arg Ala Arg Gly Tyr
305                 310

<210> SEQ ID NO 7
<211> LENGTH: 1083
<212> TYPE: DNA
<213> ORGANISM: Escherichia coli

<400> SEQUENCE: 7

| | | | | | |
|---|---|---|---|---|---|
| gtgaaaccag | taacgttata | cgatgtcgca | gagtatgccg | gtgtctctta | tcagaccgtt | 60 |
| tcccgcgtgg | tgaaccaggc | cagccacgtt | tctgcgaaaa | cgcgggaaaa | agtggaagcg | 120 |
| gcgatggcgg | agctgaatta | cattcccaac | cgcgtggcac | aacaactggc | gggcaaacag | 180 |
| tcgttgctga | ttggcgttgc | cacctccagt | ctggccctgc | acgcgccgtc | gcaaattgtc | 240 |
| gcggcgatta | aatctcgcgc | cgatcaactg | ggtgccagcg | tggtggtgtc | gatggtagaa | 300 |
| cgaagcggcg | tcgaagcctg | taaagcggcg | gtgcacaatc | ttctcgcgca | acgcgtcagt | 360 |
| gggctgatca | ttaactatcc | gctggatgac | caggatgcca | ttgctgtgga | agctgcctgc | 420 |
| actaatgttc | cggcgttatt | tcttgatgtc | tctgaccaga | cacccatcaa | cagtattatt | 480 |
| ttctcccatg | aagacggtac | gcgactgggc | gtggagcatc | tggtcgcatt | gggtcaccag | 540 |
| caaatcgcgc | tgttagcggg | cccattaagt | tctgtctcgg | cgcgtctgcg | tctggctggc | 600 |
| tggcataaat | atctcactcg | caatcaaatt | cagccgatag | cggaacggga | aggcgactgg | 660 |
| agtgccatgt | ccggttttca | acaaaccatg | caaatgctga | atgagggcat | cgttcccact | 720 |
| gcgatgctgg | ttgccaacga | tcagatggcg | ctgggcgcaa | tgcgcgccat | taccgagtcc | 780 |
| gggctgcgcg | ttggtgcgga | tatctcggta | gtgggatacg | acgataccga | agacagctca | 840 |
| tgttatatcc | cgccgttaac | caccatcaaa | caggattttc | gcctgctggg | gcaaaccagc | 900 |
| gtggaccgct | tgctgcaact | ctctcagggc | caggcggtga | agggcaatca | gctgttgccc | 960 |
| gtctcactgg | tgaaaagaaa | aaccacccctg | gcgcccaata | cgcaaaccgc | ctctccccgc | 1020 |
| gcgttggccg | attcattaat | gcagctggca | cgacaggttt | cccgactgga | aagcgggcag | 1080 |
| tga | | | | | | 1083 |

<210> SEQ ID NO 8
<211> LENGTH: 360
<212> TYPE: PRT
<213> ORGANISM: Escherichia coli

<400> SEQUENCE: 8

Met Lys Pro Val Thr Leu Tyr Asp Val Ala Glu Tyr Ala Gly Val Ser

```
  1               5                   10                  15
Tyr Gln Thr Val Ser Arg Val Val Asn Gln Ala Ser His Val Ser Ala
                20                  25                  30

Lys Thr Arg Glu Lys Val Glu Ala Ala Met Ala Glu Leu Asn Tyr Ile
            35                  40                  45

Pro Asn Arg Val Ala Gln Gln Leu Ala Gly Lys Gln Ser Leu Leu Ile
        50                  55                  60

Gly Val Ala Thr Ser Ser Leu Ala Leu His Ala Pro Ser Gln Ile Val
 65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360

<210> SEQ ID NO 9
<211> LENGTH: 82
<212> TYPE: DNA
<213> ORGANISM: Artificial Sequence
<220> FEATURE:
<223> OTHER INFORMATION: primer for ycdW deletion

<400> SEQUENCE: 9
atgagaataa atttcgcaca acgcttttcg ggagtcagta tggatatcat cttttatcac    60
```

```
ccaacgttcg atacccaatg gg                                              82
```

<210> SEQ ID NO 10
<211> LENGTH: 79
<212> TYPE: DNA
<213> ORGANISM: Artificial Sequence
<220> FEATURE:
<223> OTHER INFORMATION: primer for ycdW deletion

<400> SEQUENCE: 10

```
ttagtagccg cgtgcgcggt cgacttgccc gcagaccctc tcccttttt cgagctgggc     60 aatggtgcga gaaatgtac                                                 79
```

<210> SEQ ID NO 11
<211> LENGTH: 1305
<212> TYPE: DNA
<213> ORGANISM: Escherichia coli

<400> SEQUENCE: 11

```
atgaaaaccc gtacacaaca aattgaagaa ttacagaaag agtggactca accgcgttgg     60
gaaggcatta ctcgcccata cagtgcggaa gatgtggtga aattacgcgg ttcagtcaat    120
cctgaatgca cgctggcgca actgggcgca gcgaaaatgt ggcgtctgct gcacggtgag    180
tcgaaaaaag gctacatcaa cagcctcggc gcactgactg gcggtcaggc gctgcaacag    240
gcgaaagcgg gtattgaagc agtctatctg tcgggatggc aggtagcggc ggacgctaac    300
ctggcggcca gcatgtatcc ggatcagtcg ctctatccgg caaactcggt gccagctgtg    360
gtggagcgga tcaacaacac cttccgtcgt gccgatcaga tccaatggtc cgcgggcatt    420
gagccgggcg atccgcgcta tgtcgattac ttcctgccga tcgttgccga tgcggaagcc    480
ggttttggcg gtgtcctgaa tgcctttgaa ctgatgaaag cgatgattga agccggtgca    540
gcggcagttc acttcgaaga tcagctggcg tcagtgaaga atgcggtca catgggcggc    600 aaagttttag tgccaactca ggaagctatt cagaaactgg tcgcggcgcg tctggcagct    660
gacgtgacgg cgttccaac cctgctggtt gcccgtaccg atgctgatgc ggcggatctg    720
atcacctccg attgcgaccc gtatgacagc gaatttatta ccggcgagcg taccagtgaa    780
ggcttcttcc gtactcatgc gggcattgag caagcgatca gccgtggcct ggcgtatgcg    840
ccatatgctg acctggtctg gtgtgaaacc tccacgccgg atctggaact ggcgcgtcgc    900
tttgcacaag ctatccacgc gaaatatccc ggcaaactgc tggcttataa ctgctcgccg    960
tcgttcaact ggcagaaaaa cctcgacgac aaaactattg ccagcttcca gcagcagctg   1020
tcggatatgg gctacaagtt ccagttcatc accctggcag gtatccacag catgtggttc   1080
aacatgtttg acctgcaaa cgcctatgcc cagggcgagg gtatgaagca ctacgttgag   1140
aaagtgcagc agccggaatt tgccgccgcg aaagatggct ataccttcgt atctcaccag   1200
caggaagtgg gtacaggtta cttcgataaa gtgacgacta ttattcaggg cggcacgtct   1260
tcagtcaccg cgctgaccgg ctccactgaa gaatcgcagt tctaa                   1305
```

<210> SEQ ID NO 12
<211> LENGTH: 434
<212> TYPE: PRT
<213> ORGANISM: Escherichia coli

<400> SEQUENCE: 12

```
Met Lys Thr Arg Thr Gln Gln Ile Glu Glu Leu Gln Lys Glu Trp Thr
1               5                   10                  15
```

```
Gln Pro Arg Trp Glu Gly Ile Thr Arg Pro Tyr Ser Ala Glu Asp Val
            20                  25                  30

Val Lys Leu Arg Gly Ser Val Asn Pro Glu Cys Thr Leu Ala Gln Leu
        35                  40                  45

Gly Ala Ala Lys Met Trp Arg Leu Leu His Gly Glu Ser Lys Lys Gly
    50                  55                  60

Tyr Ile Asn Ser Leu Gly Ala Leu Thr Gly Gly Gln Ala Leu Gln Gln
65                  70                  75                  80

Ala Lys Ala Gly Ile Glu Ala Val Tyr Leu Ser Gly Trp Gln Val Ala
                85                  90                  95

Ala Asp Ala Asn Leu Ala Ala Ser Met Tyr Pro Asp Gln Ser Leu Tyr
            100                 105                 110

Pro Ala Asn Ser Val Pro Ala Val Val Glu Arg Ile Asn Asn Thr Phe
        115                 120                 125

Arg Arg Ala Asp Gln Ile Gln Trp Ser Ala Gly Ile Glu Pro Gly Asp
    130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ala Met Ile
                165                 170                 175

Glu Ala Gly Ala Ala Ala Val His Phe Glu Asp Gln Leu Ala Ser Val
            180                 185                 190

Lys Lys Cys Gly His Met Gly Gly Lys Val Leu Val Pro Thr Gln Glu
        195                 200                 205

Ala Ile Gln Lys Leu Val Ala Ala Arg Leu Ala Ala Asp Val Thr Gly
    210                 215                 220

Val Pro Thr Leu Leu Val Ala Arg Thr Asp Ala Asp Ala Ala Asp Leu
225                 230                 235                 240

Ile Thr Ser Asp Cys Asp Pro Tyr Asp Ser Glu Phe Ile Thr Gly Glu
                245                 250                 255

Arg Thr Ser Glu Gly Phe Phe Arg Thr His Ala Gly Ile Glu Gln Ala
            260                 265                 270

Ile Ser Arg Gly Leu Ala Tyr Ala Pro Tyr Ala Asp Leu Val Trp Cys
        275                 280                 285

Glu Thr Ser Thr Pro Asp Leu Glu Leu Ala Arg Arg Phe Ala Gln Ala
    290                 295                 300

Ile His Ala Lys Tyr Pro Gly Lys Leu Leu Ala Tyr Asn Cys Ser Pro
305                 310                 315                 320

Ser Phe Asn Trp Gln Lys Asn Leu Asp Asp Lys Thr Ile Ala Ser Phe
                325                 330                 335

Gln Gln Gln Leu Ser Asp Met Gly Tyr Lys Phe Gln Phe Ile Thr Leu
            340                 345                 350

Ala Gly Ile His Ser Met Trp Phe Asn Met Phe Asp Leu Ala Asn Ala
        355                 360                 365

Tyr Ala Gln Gly Glu Gly Met Lys His Tyr Val Glu Lys Val Gln Gln
    370                 375                 380

Pro Glu Phe Ala Ala Lys Asp Gly Tyr Thr Phe Val Ser His Gln
385                 390                 395                 400

Gln Glu Val Gly Thr Gly Tyr Phe Asp Lys Val Thr Ile Ile Gln
                405                 410                 415

Gly Gly Thr Ser Ser Val Thr Ala Leu Thr Gly Ser Thr Glu Glu Ser
            420                 425                 430
```

Gln Phe

<210> SEQ ID NO 13
<211> LENGTH: 1602
<212> TYPE: DNA
<213> ORGANISM: Escherichia coli

<400> SEQUENCE: 13

| | | | | | |
|---|---|---|---|---|---|
| atgactgaac | aggcaacaac | aaccgatgaa | ctggctttca | caaggccgta | tggcgagcag | 60 |
| gagaagcaaa | ttcttactgc | cgaagcggta | gaatttctga | ctgagctggt | gacgcatttt | 120 |
| acgccacaac | gcaataaact | tctggcagcg | cgcattcagc | agcagcaaga | tattgataac | 180 |
| ggaacgttgc | ctgattttat | ttcggaaaca | gcttccattc | gcgatgctga | ttggaaaatt | 240 |
| cgcgggattc | ctgcggactt | agaagaccgc | cgcgtagaga | taactggccc | ggtagagcgc | 300 |
| aagatggtga | tcaacgcgct | caacgccaat | gtgaaagtct | ttatggccga | tttcgaagat | 360 |
| tcactggcac | cagactggaa | caaagtgatc | gacgggcaaa | ttaacctgcg | tgatgcggtt | 420 |
| aacggcacca | tcagttacac | caatgaagca | ggcaaaattt | accagctcaa | gcccaatcca | 480 |
| gcggttttga | tttgtcgggt | acgcggtctg | cacttgccgg | aaaaacatgt | cacctggcgt | 540 |
| ggtgaggcaa | tccccggcag | cctgtttgat | tttgcgctct | atttcttcca | caactatcag | 600 |
| gcactgttgg | caagggcag | tggtccctat | ttctatctgc | cgaaaaccca | gtcctggcag | 660 |
| gaagcggcct | ggtggagcga | agtcttcagc | tatgcagaag | atcgctttaa | tctgccgcgc | 720 |
| ggcaccatca | aggcgacgtt | gctgattgaa | acgctgcccg | ccgtgttcca | gatggatgaa | 780 |
| atccttcacg | cgctgcgtga | ccatattgtt | ggtctgaact | gcggtcgttg | ggattacatc | 840 |
| ttcagctata | tcaaaacgtt | gaaaaactat | cccgatcgcg | tcctgccaga | cagacaggca | 900 |
| gtgacgatga | taaaccatt | cctgaatgct | tactcacgcc | tgttgattaa | aacctgccat | 960 |
| aaacgcggtg | cttttgcgat | gggcggcatg | gcggcgttta | ttccgagcaa | agatgaagag | 1020 |
| cacaataacc | aggtgctcaa | caaagtaaaa | gcggataaat | cgctggaagc | caataacggt | 1080 |
| cacgatggca | catggatcgc | tcacccaggc | cttgcggaca | cggcaatggc | ggtattcaac | 1140 |
| gacattctcg | gctcccgtaa | aaatcagctt | gaagtgatgc | gcgaacaaga | cgcgccgatt | 1200 |
| actgccgatc | agctgctggc | accttgtgat | ggtgaacgca | ccgaagaagg | tatgcgcgcc | 1260 |
| aacattcgcg | tggctgtgca | gtacatcgaa | gcgtggatct | ctggcaacgg | ctgtgtgccg | 1320 |
| atttatggcc | tgatggaaga | tgcggcgacg | gctgaaattt | cccgtacctc | gatctggcag | 1380 |
| tggatccatc | atcaaaaaac | gttgagcaat | ggcaaaccgg | tgaccaaagc | cttgttccgc | 1440 |
| cagatgctgg | gcgaagagat | gaaagtcatt | gccagcgaac | tgggcgaaga | acgtttctcc | 1500 |
| cagggggcgtt | ttgacgatgc | cgcacgcttg | atggaacaga | tcaccacttc | cgatgagtta | 1560 |
| attgatttcc | tgaccctgcc | aggctaccgc | ctgttagcgt | aa | | 1602 |

<210> SEQ ID NO 14
<211> LENGTH: 533
<212> TYPE: PRT
<213> ORGANISM: Escherichia coli

<400> SEQUENCE: 14

Met Thr Glu Gln Ala Thr Thr Thr Asp Glu Leu Ala Phe Thr Arg Pro
1               5                   10                  15

Tyr Gly Glu Gln Glu Lys Gln Ile Leu Thr Ala Glu Ala Val Glu Phe
            20                  25                  30

Leu Thr Glu Leu Val Thr His Phe Thr Pro Gln Arg Asn Lys Leu Leu

```
                35                  40                  45
Ala Ala Arg Ile Gln Gln Gln Asp Ile Asp Asn Gly Thr Leu Pro
 50                  55                  60

Asp Phe Ile Ser Glu Thr Ala Ser Ile Arg Asp Ala Asp Trp Lys Ile
65                   70                  75                  80

Arg Gly Ile Pro Ala Asp Leu Glu Asp Arg Val Glu Ile Thr Gly
                 85                  90                  95

Pro Val Glu Arg Lys Met Val Ile Asn Ala Leu Asn Ala Asn Val Lys
                100                 105                 110

Val Phe Met Ala Asp Phe Glu Asp Ser Leu Ala Pro Asp Trp Asn Lys
             115                 120                 125

Val Ile Asp Gly Gln Ile Asn Leu Arg Asp Ala Val Asn Gly Thr Ile
         130                 135                 140

Ser Tyr Thr Asn Glu Ala Gly Lys Ile Tyr Gln Leu Lys Pro Asn Pro
145                 150                 155                 160

Ala Val Leu Ile Cys Arg Val Arg Gly Leu His Leu Pro Glu Lys His
                165                 170                 175

Val Thr Trp Arg Gly Glu Ala Ile Pro Gly Ser Leu Phe Asp Phe Ala
             180                 185                 190

Leu Tyr Phe Phe His Asn Tyr Gln Ala Leu Leu Ala Lys Gly Ser Gly
         195                 200                 205

Pro Tyr Phe Tyr Leu Pro Lys Thr Gln Ser Trp Gln Glu Ala Ala Trp
     210                 215                 220

Trp Ser Glu Val Phe Ser Tyr Ala Glu Asp Arg Phe Asn Leu Pro Arg
225                 230                 235                 240

Gly Thr Ile Lys Ala Thr Leu Leu Ile Glu Thr Leu Pro Ala Val Phe
                245                 250                 255

Gln Met Asp Glu Ile Leu His Ala Leu Arg Asp His Ile Val Gly Leu
             260                 265                 270

Asn Cys Gly Arg Trp Asp Tyr Ile Phe Ser Tyr Ile Lys Thr Leu Lys
         275                 280                 285

Asn Tyr Pro Asp Arg Val Leu Pro Asp Arg Gln Ala Val Thr Met Asp
     290                 295                 300

Lys Pro Phe Leu Asn Ala Tyr Ser Arg Leu Leu Ile Lys Thr Cys His
305                 310                 315                 320

Lys Arg Gly Ala Phe Ala Met Gly Gly Met Ala Ala Phe Ile Pro Ser
                325                 330                 335

Lys Asp Glu Glu His Asn Asn Gln Val Leu Asn Lys Val Lys Ala Asp
             340                 345                 350

Lys Ser Leu Glu Ala Asn Asn Gly His Asp Gly Thr Trp Ile Ala His
         355                 360                 365

Pro Gly Leu Ala Asp Thr Ala Met Ala Val Phe Asn Asp Ile Leu Gly
     370                 375                 380

Ser Arg Lys Asn Gln Leu Glu Val Met Arg Glu Gln Asp Ala Pro Ile
385                 390                 395                 400

Thr Ala Asp Gln Leu Leu Ala Pro Cys Asp Gly Glu Arg Thr Glu Glu
                405                 410                 415

Gly Met Arg Ala Asn Ile Arg Val Ala Val Gln Tyr Ile Glu Ala Trp
             420                 425                 430

Ile Ser Gly Asn Gly Cys Val Pro Ile Tyr Gly Leu Met Glu Asp Ala
         435                 440                 445

Ala Thr Ala Glu Ile Ser Arg Ser Ile Trp Gln Trp Ile His His
     450                 455                 460
```

Gln Lys Thr Leu Ser Asn Gly Lys Pro Val Thr Lys Ala Leu Phe Arg
465                 470                 475                 480

Gln Met Leu Gly Glu Glu Met Lys Val Ile Ala Ser Glu Leu Gly Glu
            485                 490                 495

Glu Arg Phe Ser Gln Gly Arg Phe Asp Asp Ala Ala Arg Leu Met Glu
        500                 505                 510

Gln Ile Thr Thr Ser Asp Glu Leu Ile Asp Phe Leu Thr Leu Pro Gly
            515                 520                 525

Tyr Arg Leu Leu Ala
    530

<210> SEQ ID NO 15
<211> LENGTH: 80
<212> TYPE: DNA
<213> ORGANISM: Artificial Sequence
<220> FEATURE:
<223> OTHER INFORMATION: primer for aceBAK deletion

<400> SEQUENCE: 15
ctggctttca caaggccgta tggcgagcag gagaagcaaa ttcttactgc cgaagcggta    60
gaatttctga ctgagctggt                                                80

<210> SEQ ID NO 16
<211> LENGTH: 79
<212> TYPE: DNA
<213> ORGANISM: Artificial Sequence
<220> FEATURE:
<223> OTHER INFORMATION: primer for aceBAK deletion

<400> SEQUENCE: 16
aacatcttcc acatgcccttt cacgtatgcg gttttgtagt gcgcgccagt aatcagcgcg    60
gaacaggtcg gcgtgcatc                                                 79

<210> SEQ ID NO 17
<211> LENGTH: 1203
<212> TYPE: DNA
<213> ORGANISM: Escherichia coli

<400> SEQUENCE: 17
atgtcgagta agttagtact ggttctgaac tgcggtagtt cttcactgaa atttgccatc    60
atcgatgcag taaatggtga agagtacctt tctggtttag ccgaatgttt ccacctgccc   120
gaagcacgta tcaaatggaa aatggacggc aataaacagg aagcggcttt aggtgcaggc   180
gccgctcaca gcgaagcgct caactttatc gttaatacta ttctggcaca aaaaccagaa   240
ctgtctgcgc agctgactgc tatcggtcac cgtatcgtac acggcggcga aaagtatacc   300
agctccgtag tgatcgatga gtctgttatt cagggtatca agatgcagc ttcttttgca   360 ccgctgcaca cccggctca cctgatcggt atcgaagaag ctctgaaatc tttcccacag   420
ctgaaagaca aaaacgttgc tgtatttgac accgcgttcc accagactat gccggaagag   480
tcttacctct acgccctgcc ttacaacctg tacaagagc acggcatccg tcgttacggc   540
gcgcacggca ccagccactt ctatgtaacc caggaagcgg caaaaatgct gaacaaaccg   600
gtagaagaac tgaacatcat cacctgccac ctgggcaacg gtggttccgt ttctgctatc   660
cgcaacggta atgcgttgga cacctctatg ggcctgaccc cgctggaagg tctggtcatg   720
ggtacccgtt ctggtgatat cgatccggcg atcatcttcc acctgcacga cacccctgggc   780 atgagcgttg acgcaatcaa caaactgctg accaaagagt ctggcctgct gggtctgacc   840

```
gaagtgacca gcgactgccg ctatgttgaa gacaactacg cgacgaaaga agacgcgaag    900
cgcgcaatgg acgtttactg ccaccgcctg gcgaaataca tcggtgccta cactgcgctg    960
atggatggtc gtctggacgc tgttgtattc actggtggta tcggtgaaaa tgccgcaatg   1020
gttcgtgaac tgtctctggg caaactgggc gtgctgggct ttgaagttga tcatgaacgc   1080
aacctggctg cacgtttcgg caaatctggt ttcatcaaca agaaggtac ccgtcctgcg    1140 gtggttatcc caaccaacga gaactggtt atcgcgcaag acgcgagccg cctgactgcc    1200
tga                                                                 1203
```

<210> SEQ ID NO 18
<211> LENGTH: 400
<212> TYPE: PRT
<213> ORGANISM: Escherichia coli

<400> SEQUENCE: 18

```
Met Ser Ser Lys Leu Val Leu Val Leu Asn Cys Gly Ser Ser Ser Leu
1               5                   10                  15

Lys Phe Ala Ile Ile Asp Ala Val Asn Gly Glu Glu Tyr Leu Ser Gly
                20                  25                  30

Leu Ala Glu Cys Phe His Leu Pro Glu Ala Arg Ile Lys Trp Lys Met
            35                  40                  45

Asp Gly Asn Lys Gln Glu Ala Ala Leu Gly Ala Gly Ala Ala His Ser
        50                  55                  60

Glu Ala Leu Asn Phe Ile Val Asn Thr Ile Leu Ala Gln Lys Pro Glu
65                  70                  75                  80

Leu Ser Ala Gln Leu Thr Ala Ile Gly His Arg Ile Val His Gly Gly
                85                  90                  95

Glu Lys Tyr Thr Ser Ser Val Val Ile Asp Glu Ser Val Ile Gln Gly
                100                 105                 110

Ile Lys Asp Ala Ala Ser Phe Ala Pro Leu His Asn Pro Ala His Leu
            115                 120                 125

Ile Gly Ile Glu Glu Ala Leu Lys Ser Phe Pro Gln Leu Lys Asp Lys
        130                 135                 140

Asn Val Ala Val Phe Asp Thr Ala Phe His Gln Thr Met Pro Glu Glu
145                 150                 155                 160

Ser Tyr Leu Tyr Ala Leu Pro Tyr Asn Leu Tyr Lys Glu His Gly Ile
                165                 170                 175

Arg Arg Tyr Gly Ala His Gly Thr Ser His Phe Tyr Val Thr Gln Glu
            180                 185                 190

Ala Ala Lys Met Leu Asn Lys Pro Val Glu Glu Leu Asn Ile Ile Thr
        195                 200                 205

Cys His Leu Gly Asn Gly Gly Ser Val Ser Ala Ile Arg Asn Gly Lys
    210                 215                 220

Cys Val Asp Thr Ser Met Gly Leu Thr Pro Leu Glu Gly Leu Val Met
225                 230                 235                 240

Gly Thr Arg Ser Gly Asp Ile Asp Pro Ala Ile Ile Phe His Leu His
                245                 250                 255

Asp Thr Leu Gly Met Ser Val Asp Ala Ile Asn Lys Leu Leu Thr Lys
            260                 265                 270

Glu Ser Gly Leu Leu Gly Leu Thr Glu Val Thr Ser Asp Cys Arg Tyr
        275                 280                 285

Val Glu Asp Asn Tyr Ala Thr Lys Glu Asp Ala Lys Arg Ala Met Asp
    290                 295                 300
```

| Val | Tyr | Cys | His | Arg | Leu | Ala | Lys | Tyr | Ile | Gly | Ala | Tyr | Thr | Ala | Leu |
| 305 | | | | 310 | | | | | 315 | | | | | 320 | |

| Met | Asp | Gly | Arg | Leu | Asp | Ala | Val | Val | Phe | Thr | Gly | Gly | Ile | Gly | Glu |
| | | | 325 | | | | | 330 | | | | | 335 | | |

| Asn | Ala | Ala | Met | Val | Arg | Glu | Leu | Ser | Leu | Gly | Lys | Leu | Gly | Val | Leu |
| | | 340 | | | | | 345 | | | | | 350 | | | |

| Gly | Phe | Glu | Val | Asp | His | Glu | Arg | Asn | Leu | Ala | Ala | Arg | Phe | Gly | Lys |
| | 355 | | | | | 360 | | | | | 365 | | | | |

| Ser | Gly | Phe | Ile | Asn | Lys | Glu | Gly | Thr | Arg | Pro | Ala | Val | Val | Ile | Pro |
| 370 | | | | | 375 | | | | | 380 | | | | | |

| Thr | Asn | Glu | Glu | Leu | Val | Ile | Ala | Gln | Asp | Ala | Ser | Arg | Leu | Thr | Ala |
| 385 | | | | | 390 | | | | | 395 | | | | | 400 |

<210> SEQ ID NO 19
<211> LENGTH: 2145
<212> TYPE: DNA
<213> ORGANISM: Escherichia coli

<400> SEQUENCE: 19

```
gtgtcccgta ttattatgct gatccctacc ggaaccagcg tcggtctgac cagcgtcagc      60
cttggcgtga tccgtgcaat ggaacgcaaa ggcgttcgtc tgagcgtttt caaacctatc     120
gctcagccgc gtaccggtgg cgatgcgccc gatcagacta cgactatcgt gcgtgcgaac     180
tcttccacca cgacggccgc tgaaccgctg aaaatgagct acgttgaagg tctgctttcc     240
agcaatcaga aagatgtgct gatggaagag atcgtcgcaa actaccacgc taacaccaaa     300
gacgctgaag tcgttctggt tgaaggtctg gtcccgacac gtaagcacca gtttgcccag     360
tctctgaact acgaaatcgc taaaacgctg aatgcggaaa tcgtcttcgt tatgtctcag     420
ggcactgaca ccccggaaca gctgaaagag cgtatcgaac tgacccgcaa cagcttcggc     480
ggtgccaaaa acaccaacat caccggcgtt atcgttaaca aactgaacgc accggttgat     540
gaacagggtc gtactcgccc ggatctgtcc gagattttcg acgactcttc caaagctaaa     600
gtaaacaatg ttgatccggc gaagctgcaa gaatccagcc cgctgccggt tctcggcgct     660
gtgccgtgga gctttgacct gatcgcgact cgtgcgatca atatggctcg ccacctgaat     720
gcgaccatca tcaacgaagg cgacatcaat actcgccgcg ttaaatccgt cactttctgc     780
gcacgcagca ttccgcacat gctggagcac ttccgtgccg ttctctgct ggtgacttcc     840
gcagaccgtc ctgacgtgct ggtggccgct tgcctggcag ccatgaacgg cgtagaaatc     900
ggtgccctgc tgctgactgg cggttacgaa atggacgcgc gcatttctaa actgtgcgaa     960
cgtgctttcg ctaccggcct gccggtattt atggtgaaca ccaacacctg gcagacctct    1020
ctgagcctgc tgagcttcaa cctggaagtt ccggttgacg atcacgaacg tatcgagaaa    1080
gttcaggaat acgttgctaa ctacatcaac gctgactgga tcgaatctct gactgccact    1140
tctgagcgca gccgtcgtct gtctccgcct gcgttccgtt atcagctgac tgaacttgcg    1200
cgcaaagcgg gcaaacgtat cgtactgccg gaaggtgacg aaccgcgtac cgttaaagca    1260
gccgctatct gtgctgaacg tggtatcgca acttgcgtac tgctgggtaa tccggcagag    1320
atcaaccgtg ttgcagcgtc tcagggtgta gaactgggtg cagggattga aatcgttgat    1380
ccagaagtgg ttcgcgaaag ctatgttggt cgtctggtcg aactgcgtaa gaacaaaggc    1440
atgaccgaaa ccgttgcccg cgaacagctg gaagacaacg tggtgctcgg tacgctgatg    1500
ctggaacagg atgaagttga tggtctggtt tccggtgctg ttcacactac cgcaaacacc    1560
```

-continued

```
atccgtccgc cgctgcagct gatcaaaact gcaccgggca gctccctggt atcttccgtg   1620
ttcttcatgc tgctgccgga acaggtttac gtttacggtg actgtgcgat caacccggat   1680
ccgaccgctg aacagctggc agaaatcgcg attcagtccg ctgattccgc tgcggccttc   1740
ggtatcgaac cgcgcgttgc tatgctctcc tactccaccg gtacttctgg tgcaggtagc   1800
gacgtagaaa aagttcgcga agcaactcgt ctggcgcagg aaaaacgtcc tgacctgatg   1860
atcgacggtc cgctgcagta cgacgctgcg gtaatggctg acgttgcgaa atccaaagcg   1920
ccgaactctc cggttgcagg tcgcgctacc gtgttcatct cccggatct gaacaccggt    1980 aacaccacct acaaagcggt acagcgttct gccgacctga tctccatcgg gcgatgctg    2040 cagggtatgc gcaagccggt taacgacctg tcccgtggcg cactggttga cgatatcgtc   2100
tacaccatcg cgctgactgc gattcagtct gcacagcagc agtaa                   2145
```

```
<210> SEQ ID NO 20
<211> LENGTH: 714
<212> TYPE: PRT
<213> ORGANISM: Escherichia coli

<400> SEQUENCE: 20
```

```
Met Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp
        35                  40                  45

Ala Pro Asp Gln Thr Thr Thr Ile Val Arg Ala Asn Ser Ser Thr Thr
    50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
    130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Asp Pro Ala Lys
        195                 200                 205

Leu Gln Glu Ser Ser Pro Leu Pro Val Leu Gly Ala Val Pro Trp Ser
    210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
            260                 265                 270
```

```
Ala Gly Ser Leu Leu Val Thr Ser Ala Asp Arg Pro Asp Val Leu Val
            275                 280                 285

Ala Ala Cys Leu Ala Ala Met Asn Gly Val Glu Ile Gly Ala Leu Leu
        290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
            340                 345                 350

Asp Asp His Glu Arg Ile Glu Lys Val Gln Glu Tyr Val Ala Asn Tyr
        355                 360                 365

Ile Asn Ala Asp Trp Ile Glu Ser Leu Thr Ala Thr Ser Glu Arg Ser
370                 375                 380

Arg Arg Leu Ser Pro Pro Ala Phe Arg Tyr Gln Leu Thr Glu Leu Ala
385                 390                 395                 400

Arg Lys Ala Gly Lys Arg Ile Val Leu Pro Glu Gly Asp Glu Pro Arg
                405                 410                 415

Thr Val Lys Ala Ala Ile Cys Ala Glu Arg Gly Ile Ala Thr Cys
            420                 425                 430

Val Leu Leu Gly Asn Pro Ala Glu Ile Asn Arg Val Ala Ala Ser Gln
        435                 440                 445

Gly Val Glu Leu Gly Ala Gly Ile Glu Ile Val Asp Pro Glu Val Val
450                 455                 460

Arg Glu Ser Tyr Val Gly Arg Leu Val Glu Leu Arg Lys Asn Lys Gly
465                 470                 475                 480

Met Thr Glu Thr Val Ala Arg Glu Gln Leu Glu Asp Asn Val Val Leu
                485                 490                 495

Gly Thr Leu Met Leu Glu Gln Asp Glu Val Asp Gly Leu Val Ser Gly
            500                 505                 510

Ala Val His Thr Thr Ala Asn Thr Ile Arg Pro Pro Leu Gln Leu Ile
        515                 520                 525

Lys Thr Ala Pro Gly Ser Ser Leu Val Ser Ser Val Phe Phe Met Leu
530                 535                 540

Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
                565                 570                 575

Ala Ala Ala Phe Gly Ile Glu Pro Arg Val Ala Met Leu Ser Tyr Ser
            580                 585                 590

Thr Gly Thr Ser Gly Ala Gly Ser Asp Val Glu Lys Val Arg Glu Ala
        595                 600                 605

Thr Arg Leu Ala Gln Glu Lys Arg Pro Asp Leu Met Ile Asp Gly Pro
610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
                645                 650                 655

Leu Asn Thr Gly Asn Thr Thr Tyr Lys Ala Val Gln Arg Ser Ala Asp
            660                 665                 670

Leu Ile Ser Ile Gly Pro Met Leu Gln Gly Met Arg Lys Pro Val Asn
        675                 680                 685

Asp Leu Ser Arg Gly Ala Leu Val Asp Asp Ile Val Tyr Thr Ile Ala
```

Leu Thr Ala Ile Gln Ser Ala Gln Gln Gln
705              710

<210> SEQ ID NO 21
<211> LENGTH: 2478
<212> TYPE: DNA
<213> ORGANISM: Bifidobacterium animalis

<400> SEQUENCE: 21

| | | | | |
|---|---|---|---|---|
| atgactaatc | ctgttattgg | taccccatgg | cagaagctgg | accgtccggt | ttccgaagag | 60 |
| gccatcgaag | gcatggacaa | gtactggcgc | gtcgccaact | acatgtccat | cggccagatc | 120 |
| tacctgcgta | gcaacccgct | gatgaaggag | cccttcaccc | gcgatgacgt | gaagcaccgt | 180 |
| ctggtcggcc | actggggcac | caccccgggc | ctgaacttcc | ttctcgccca | tatcaaccgc | 240 |
| ctgatcgccg | atcaccagca | gaacaccgtg | ttcatcatgg | gtcctggcca | cggcggccct | 300 |
| gcaggtaccg | ctcagtccta | catcgacggc | acctacaccg | agtactaccc | gaacatcacc | 360 |
| aaggacgagg | ctggcctgca | gaagttcttc | cgccagttct | cctacccggg | tggcattcct | 420 |
| tcccacttcg | ctccggagac | gccaggctcc | atccacgaag | cggcgagct | gggctacgcc | 480 |
| ctgtcgcacg | cctacggcgc | gatcatgaac | aacccgagcc | tcttcgtccc | gtgcatcatc | 540 |
| ggtgacggcg | aagccgagac | cggccctctg | gccaccggct | ggcagtccaa | caagctcgtc | 600 |
| aacccgcgca | ccgacggcat | cgtgctgccg | atcctgcacc | tcaacggcta | caagatcgcc | 660 |
| aacccgacgc | tcctcgcccg | catctccgac | gaggagctgc | acgacttctt | ccgcggtatg | 720 |
| ggttaccacc | cgtacgagtt | cgtcgccggc | ttcgacaacg | aggatcacct | gtcgatccac | 780 |
| cgtcgcttcg | ccgagctctt | cgagaccatc | ttcgacgaga | tctgcgatat | caaggctgcg | 840 |
| gctcagaccg | acgacatgac | ccgtccgttc | tacccgatgc | tcatcttccg | cacccccgaag | 900 |
| ggctggacct | gcccgaagtt | catcgacggc | aagaagaccg | aaggctcctg | gcgtgcacac | 960 |
| caggtcccgc | tggcttccgc | ccgcgacacc | gaggcccact | cgaagtcct | caagggctgg | 1020 |
| atggaatcct | acaagccgga | ggagctcttc | aacgccgacg | gctccatcaa | ggacgacgtc | 1080 |
| accgcattca | tgcctaaggg | cgaactgcgc | atcgcgcca | cccgaacgc | caacggtggc | 1140 |
| cgcatccgcg | aggatctgaa | gctccctgag | ctcgatcagt | acgagatcac | cggcgtcaag | 1200 |
| gaatacggcc | atggctgggg | ccaggtcgag | gctccgcgct | ccctcggcgc | gtactgccgc | 1260 |
| gacatcatca | gaacaaccc | ggattcgttc | cgcatcttcg | gacctgatga | gaccgcatcc | 1320 |
| aaccgtctga | acgcgaccta | cgaggtcacc | aagaagcagt | gggacaacgg | ctatctctcg | 1380 |
| gctctcgtcg | acgagaacat | ggctgtcacc | ggccaggttg | tcgagcagct | ctccgagcat | 1440 |
| cagtgcgaag | gcttcctcga | ggcctacctg | ctcacgggcc | gccacggcat | gtggagcacc | 1500 |
| tatgagtcct | tcgcccacgt | gatcgactcg | atgctcaacc | agcatgcgaa | gtggctcgag | 1560 |
| gcgaccgtcc | gcgagatccc | gtggcgcaag | ccgatctcct | cggtcaacct | cctcgtctcc | 1620 |
| tcgcacgtgt | ggcgtcagga | ccacaacggc | ttctcgcatc | aggacccggg | tgtcacctcc | 1680 |
| gtcctgatca | acaagacgtt | caacaacgac | cacgtgacga | acatctactt | cgcgaccgac | 1740 |
| gccaacatgc | tgctcgcgat | cgccgagaag | tgcttcaagt | ccaccaacaa | gatcaacgcg | 1800 |
| atcttctccg | gcaagcagcc | ggctccgacc | tggattaccc | tcgacgaggc | tcgtgccgag | 1860 |
| ctcgaggccg | gcgccgccga | gtggaagtgg | gcttccaacg | ccaagagcaa | cgacgaggtc | 1920 |
| cagattgtcc | tcgccgccgc | aggcgatgtc | ccgacccagg | agatcatggc | cgcttccgat | 1980 |

```
gccctgaaca aggatggcat caagttcaag gtcgtcaacg ttgttgacct cctgaagctg   2040
cagtccccgg agaacaacga cgaggccatg tcgaacgaag acttcaccga gctcttcacc   2100
gccgacaaac cggttctgtt cgcctaccac tcctatgccc aggacgttcg tggtcttatc   2160
tacgaccgcc cgaaccacga caacttcaac gttgtcggct acaaggagca gggctccacg   2220
accacgccgt cgacatggtc cgcgtcaac gacatggatc gctacgcgct cgaagctcag   2280
gctctcgagc tgatcgacgc cgacaagtat gccgacaaga tcgacgagct caacgcgttc   2340
cgcaagaccg cgttccagtt cgccgtcgac aacggctacg acatcccgga gttcaccgac   2400
tgggtgtacc cggacgtcaa ggtcgacgag acgcagatgc tctccgcgac cgcggcgacc   2460
gctggcgaca acgagtga                                                  2478
```

<210> SEQ ID NO 22
<211> LENGTH: 825
<212> TYPE: PRT
<213> ORGANISM: Bifidobacterium animalis

<400> SEQUENCE: 22

```
Met Thr Asn Pro Val Ile Gly Thr Pro Trp Gln Lys Leu Asp Arg Pro
1               5                   10                  15

Val Ser Glu Glu Ala Ile Glu Gly Met Asp Lys Tyr Trp Arg Val Ala
            20                  25                  30

Asn Tyr Met Ser Ile Gly Gln Ile Tyr Leu Arg Ser Asn Pro Leu Met
        35                  40                  45

Lys Glu Pro Phe Thr Arg Asp Asp Val Lys His Arg Leu Val Gly His
    50                  55                  60

Trp Gly Thr Thr Pro Gly Leu Asn Phe Leu Leu Ala His Ile Asn Arg
65                  70                  75                  80

Leu Ile Ala Asp His Gln Gln Asn Thr Val Phe Ile Met Gly Pro Gly
                85                  90                  95

His Gly Gly Pro Ala Gly Thr Ala Gln Ser Tyr Ile Asp Gly Thr Tyr
            100                 105                 110

Thr Glu Tyr Tyr Pro Asn Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asn Asn Pro Ser Leu Phe Val
                165                 170                 175

Pro Cys Ile Ile Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Leu
    210                 215                 220

Leu Ala Arg Ile Ser Asp Glu Glu Leu His Asp Phe Phe Arg Gly Met
225                 230                 235                 240

Gly Tyr His Pro Tyr Glu Phe Val Ala Gly Phe Asp Asn Glu Asp His
                245                 250                 255

Leu Ser Ile His Arg Arg Phe Ala Glu Leu Phe Glu Thr Ile Phe Asp
            260                 265                 270

Glu Ile Cys Asp Ile Lys Ala Ala Ala Gln Thr Asp Asp Met Thr Arg
        275                 280                 285
```

-continued

```
Pro Phe Tyr Pro Met Leu Ile Phe Arg Thr Pro Lys Gly Trp Thr Cys
    290                 295                 300
Pro Lys Phe Ile Asp Gly Lys Lys Thr Glu Gly Ser Trp Arg Ala His
305                 310                 315                 320
Gln Val Pro Leu Ala Ser Ala Arg Asp Thr Glu Ala His Phe Glu Val
                325                 330                 335
Leu Lys Gly Trp Met Glu Ser Tyr Lys Pro Glu Glu Leu Phe Asn Ala
                340                 345                 350
Asp Gly Ser Ile Lys Asp Val Thr Ala Phe Met Pro Lys Gly Glu
                355                 360                 365
Leu Arg Ile Gly Ala Asn Pro Asn Ala Asn Gly Gly Arg Ile Arg Glu
    370                 375                 380
Asp Leu Lys Leu Pro Glu Leu Asp Gln Tyr Glu Ile Thr Gly Val Lys
385                 390                 395                 400
Glu Tyr Gly His Gly Trp Gly Gln Val Glu Ala Pro Arg Ser Leu Gly
                405                 410                 415
Ala Tyr Cys Arg Asp Ile Ile Lys Asn Asn Pro Asp Ser Phe Arg Ile
                420                 425                 430
Phe Gly Pro Asp Glu Thr Ala Ser Asn Arg Leu Asn Ala Thr Tyr Glu
                435                 440                 445
Val Thr Lys Lys Gln Trp Asp Asn Gly Tyr Leu Ser Ala Leu Val Asp
    450                 455                 460
Glu Asn Met Ala Val Thr Gly Gln Val Val Glu Gln Leu Ser Glu His
465                 470                 475                 480
Gln Cys Glu Gly Phe Leu Glu Ala Tyr Leu Leu Thr Gly Arg His Gly
                485                 490                 495
Met Trp Ser Thr Tyr Glu Ser Phe Ala His Val Ile Asp Ser Met Leu
                500                 505                 510
Asn Gln His Ala Lys Trp Leu Glu Ala Thr Val Arg Glu Ile Pro Trp
    515                 520                 525
Arg Lys Pro Ile Ser Ser Val Asn Leu Leu Val Ser Ser His Val Trp
530                 535                 540
Arg Gln Asp His Asn Gly Phe Ser His Gln Asp Pro Gly Val Thr Ser
545                 550                 555                 560
Val Leu Ile Asn Lys Thr Phe Asn Asn Asp His Val Thr Asn Ile Tyr
                565                 570                 575
Phe Ala Thr Asp Ala Asn Met Leu Leu Ala Ile Ala Glu Lys Cys Phe
                580                 585                 590
Lys Ser Thr Asn Lys Ile Asn Ala Ile Phe Ser Gly Lys Gln Pro Ala
    595                 600                 605
Pro Thr Trp Ile Thr Leu Asp Glu Ala Arg Ala Glu Leu Glu Ala Gly
610                 615                 620
Ala Ala Glu Trp Lys Trp Ala Ser Asn Ala Lys Ser Asn Asp Glu Val
625                 630                 635                 640
Gln Ile Val Leu Ala Ala Gly Asp Val Pro Thr Gln Glu Ile Met
                645                 650                 655
Ala Ala Ser Asp Ala Leu Asn Lys Asp Gly Ile Lys Phe Lys Val Val
                660                 665                 670
Asn Val Val Asp Leu Leu Lys Leu Gln Ser Pro Glu Asn Asn Asp Glu
    675                 680                 685
Ala Met Ser Asn Glu Asp Phe Thr Glu Leu Phe Thr Ala Asp Lys Pro
690                 695                 700
```

```
Val Leu Phe Ala Tyr His Ser Tyr Ala Gln Asp Val Arg Gly Leu Ile
705                 710                 715                 720

Tyr Asp Arg Pro Asn His Asp Asn Phe Asn Val Val Gly Tyr Lys Glu
            725                 730                 735

Gln Gly Ser Thr Thr Thr Pro Phe Asp Met Val Arg Val Asn Asp Met
            740                 745                 750

Asp Arg Tyr Ala Leu Glu Ala Gln Ala Leu Glu Leu Ile Asp Ala Asp
            755                 760                 765

Lys Tyr Ala Asp Lys Ile Asp Glu Leu Asn Ala Phe Arg Lys Thr Ala
    770                 775                 780

Phe Gln Phe Ala Val Asp Asn Gly Tyr Asp Ile Pro Glu Phe Thr Asp
785                 790                 795                 800

Trp Val Tyr Pro Asp Val Lys Val Asp Glu Thr Gln Met Leu Ser Ala
                805                 810                 815

Thr Ala Thr Ala Gly Asp Asn Glu
            820                 825

<210> SEQ ID NO 23
<211> LENGTH: 2478
<212> TYPE: DNA
<213> ORGANISM: Bifidobacterium adolescentis

<400> SEQUENCE: 23
atgacgagtc ctgttattgg cacccctgg aagaagctga acgctccggt ttccgaggaa      60
gctatcgaag gcgtggataa gtactggcgc gcagccaact acctctccat cggccagatc    120
tatctgcgta gcaacccgct gatgaaggag cctttcaccc gcaagacgt caagcaccgt     180 ctggtcggtc actggggcac caccccgggc ctgaacttcc tcatcggcca catcaaccgt    240
ctcattgctg atcaccagca gaacactgtg atcatcatgg gccgggcca cggcggcccg    300 gctggtaccg ctcagtccta cctggacggc acctacaccg agtacttccc gaacatcacc    360
aaggatgagg ctggcctgca gaagttcttc cgccagttct cctacccggg tgcatcccg    420 tcccactacg ctccggagac cccgggctcc atccacgaag gcggcgagct gggttacgcc    480
ctgtcccacg cctacggcgc tgtgatgaac aaccccgagcc tgttcgtccc ggccatcgtc    540
ggcgacggtg aagctgagac cggcccgctg ccaccggct ggttctccaa caagctcatc     600
aacccgcgca ccgacggtat cgtgctgccg atcctgcacc tcaacggcta caagatcgcc    660
aacccgacca tcctgtcccg catctccgac gaagagctcc acgagttctt ccacggcatg    720
ggctatgagc cgtacgagtt cgtcgctggc ttcgacaacg aggatcacct gtcgatccac    780
cgtcgtttcg ccgagctgtt cgagaccgtc ttcgacgaga tctgcgacat caaggccgcc    840
gctcagaccg acgacatgac tcgtccgttc tacccgatga tcatcttccg taccccgaag    900
ggctggacct gcccgaagtt catcgacggc aagaagaccg agggctcctg gcgttcccac    960
caggtgccgc tggcttccgc ccgcgatacc gaggcccact cgaggtcct caagaactgg   1020 ctcgagtcct acaagccgga agagctgttc gacgagaacg cgccgtgaa gccggaagtc   1080 accgccttca tgccgaccgg cgaactgcgc atcggtgaga cccgaacgc caacggtggc   1140 cgcatccgcg aagagctgaa gctgccgaag ctggaagact acgaggtcaa ggaagtcgcc   1200
gagtacggcc acggctgggg ccagctcgag gccacccgtc gtctgggcgt ctacacccgc   1260
gacatcatca gaacaaccc ggactccttc cgtatcttcg accggatga gaccgcttcc   1320 aaccgtctgc aggccgctta cgacgtcacc aacaagcagt gggacgccgg ctacctgtcc   1380
gctcaggtcg acgagcacat ggctgtcacc ggccaggtca ccgagcagct ttccgagcac   1440
```

```
cagatggaag gcttcctcga gggctacctg ctgaccggcc gtcacggcat ctggagctcc   1500
tatgagtcct tcgtgcacgt gatcgactcc atgctgaacc agcacgccaa gtggctcgag   1560
gctaccgtcc gcgagattcc gtggcgcaag ccgatctcct ccatgaacct gctcgtctcc   1620
tcccacgtgt ggcgtcagga tcacaacggc ttctcccacc aggatccggg tgtcacctcc   1680
gtcctgctga caagtgctt caacaacgat cacgtgatcg gcatctactt cccggtggat   1740
tccaacatgc tgctcgctgt ggctgagaag tgctacaagt ccaccaacaa gatcaacgcc   1800
atcatcgccg gcaagcagcc ggccgccacc tggctgaccc tggacgaagc tcgcgccgag   1860
ctcgagaagg gtgctgccga gtggaagtgg gcttccaacg tgaagtccaa cgatgaggct   1920
cagatcgtgc tcgccgccac cggtgatgtt ccgactcagg aaatcatggc cgctgccgac   1980
aagctggacg ccatgggcat caagttcaag gtcgtcaacg tggttgacct ggtcaagctg   2040
cagtccgcca aggagaacaa cgaggccctc tccgatgagg agttcgctga gctgttcacc   2100
gaggacaagc cggtcctgtt cgcttaccac tcctatgccc gcgatgtgcg tggtctgatc   2160
tacgatcgcc cgaaccacga caacttcaac gttcacggct acgaggagca gggctccacc   2220
accaccccgt acgacatggt tcgcgtgaac aacatcgatc gctacgagct ccaggctgaa   2280
gctctgcgca tgattgacgc tgacaagtac gccgacaaga tcaacgagct cgaggccttc   2340
cgtcaggaag ccttccagtt cgctgtcgac aacggctacg atcacccgga ttacaccgac   2400
tgggtctact ccggtgtcaa caccaacaag cagggtgcta tctccgctac cgccgcaacc   2460
gctggcgata acgagtga                                                 2478

<210> SEQ ID NO 24
<211> LENGTH: 825
<212> TYPE: PRT
<213> ORGANISM: Bifidobacterium adolescentis

<400> SEQUENCE: 24

Met Thr Ser Pro Val Ile Gly Thr Pro Trp Lys Lys Leu Asn Ala Pro
1               5                   10                  15

Val Ser Glu Glu Ala Ile Glu Gly Val Asp Lys Tyr Trp Arg Ala Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Ile Gly His Ile Asn Arg
65                  70                  75                  80

Leu Ile Ala Asp His Gln Gln Asn Thr Val Ile Ile Met Gly Pro Gly
                85                  90                  95

His Gly Gly Pro Ala Gly Thr Ala Gln Ser Tyr Leu Asp Gly Thr Tyr
            100                 105                 110

Thr Glu Tyr Phe Pro Asn Ile Thr Lys Asp Glu Ala Gly Leu Gln Lys
        115                 120                 125

Phe Phe Arg Gln Phe Ser Tyr Pro Gly Gly Ile Pro Ser His Tyr Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Val Met Asn Asn Pro Ser Leu Phe Val
                165                 170                 175

Pro Ala Ile Val Gly Asp Gly Glu Ala Glu Thr Gly Pro Leu Ala Thr
```

```
                180                 185                 190
Gly Trp Phe Ser Asn Lys Leu Ile Asn Pro Arg Thr Asp Gly Ile Val
            195                 200                 205
Leu Pro Ile Leu His Leu Asn Gly Tyr Lys Ile Ala Asn Pro Thr Ile
210                 215                 220
Leu Ser Arg Ile Ser Asp Glu Glu Leu His Glu Phe Phe His Gly Met
225                 230                 235                 240
Gly Tyr Glu Pro Tyr Glu Phe Val Ala Gly Phe Asp Asn Glu Asp His
                245                 250                 255
Leu Ser Ile His Arg Arg Phe Ala Glu Leu Phe Glu Thr Val Phe Asp
            260                 265                 270
Glu Ile Cys Asp Ile Lys Ala Ala Gln Thr Asp Met Thr Arg
        275                 280                 285
Pro Phe Tyr Pro Met Ile Ile Phe Arg Thr Pro Lys Gly Trp Thr Cys
    290                 295                 300
Pro Lys Phe Ile Asp Gly Lys Lys Thr Glu Gly Ser Trp Arg Ser His
305                 310                 315                 320
Gln Val Pro Leu Ala Ser Ala Arg Asp Thr Glu Ala His Phe Glu Val
                325                 330                 335
Leu Lys Asn Trp Leu Glu Ser Tyr Lys Pro Glu Glu Leu Phe Asp Glu
            340                 345                 350
Asn Gly Ala Val Lys Pro Glu Val Thr Ala Phe Met Pro Thr Gly Glu
        355                 360                 365
Leu Arg Ile Gly Glu Asn Pro Asn Ala Asn Gly Gly Arg Ile Arg Glu
    370                 375                 380
Glu Leu Lys Leu Pro Lys Leu Glu Asp Tyr Glu Val Lys Glu Val Ala
385                 390                 395                 400
Glu Tyr Gly His Gly Trp Gly Gln Leu Glu Ala Thr Arg Arg Leu Gly
                405                 410                 415
Val Tyr Thr Arg Asp Ile Ile Lys Asn Asn Pro Asp Ser Phe Arg Ile
            420                 425                 430
Phe Gly Pro Asp Glu Thr Ala Ser Asn Arg Leu Gln Ala Ala Tyr Asp
        435                 440                 445
Val Thr Asn Lys Gln Trp Asp Ala Gly Tyr Leu Ser Ala Gln Val Asp
    450                 455                 460
Glu His Met Ala Val Thr Gly Gln Val Thr Glu Gln Leu Ser Glu His
465                 470                 475                 480
Gln Met Glu Gly Phe Leu Glu Gly Tyr Leu Leu Thr Gly Arg His Gly
                485                 490                 495
Ile Trp Ser Ser Tyr Glu Ser Phe Val His Val Ile Asp Ser Met Leu
            500                 505                 510
Asn Gln His Ala Lys Trp Leu Glu Ala Thr Val Arg Glu Ile Pro Trp
        515                 520                 525
Arg Lys Pro Ile Ser Ser Met Asn Leu Leu Val Ser Ser His Val Trp
    530                 535                 540
Arg Gln Asp His Asn Gly Phe Ser His Gln Asp Pro Gly Val Thr Ser
545                 550                 555                 560
Val Leu Leu Asn Lys Cys Phe Asn Asp His Val Ile Gly Ile Tyr
                565                 570                 575
Phe Pro Val Asp Ser Asn Met Leu Leu Ala Val Ala Glu Lys Cys Tyr
            580                 585                 590
Lys Ser Thr Asn Lys Ile Asn Ala Ile Ile Ala Gly Lys Gln Pro Ala
        595                 600                 605
```

```
Ala Thr Trp Leu Thr Leu Asp Glu Ala Arg Ala Glu Leu Glu Lys Gly
        610                 615                 620

Ala Ala Glu Trp Lys Trp Ala Ser Asn Val Lys Ser Asn Asp Glu Ala
625                 630                 635                 640

Gln Ile Val Leu Ala Ala Thr Gly Asp Val Pro Thr Gln Glu Ile Met
                645                 650                 655

Ala Ala Ala Asp Lys Leu Asp Ala Met Gly Ile Lys Phe Lys Val Val
            660                 665                 670

Asn Val Val Asp Leu Val Lys Leu Gln Ser Ala Lys Glu Asn Asn Glu
        675                 680                 685

Ala Leu Ser Asp Glu Glu Phe Ala Glu Leu Phe Thr Glu Asp Lys Pro
690                 695                 700

Val Leu Phe Ala Tyr His Ser Tyr Ala Arg Asp Val Arg Gly Leu Ile
705                 710                 715                 720

Tyr Asp Arg Pro Asn His Asp Asn Phe Asn Val His Gly Tyr Glu Glu
                725                 730                 735

Gln Gly Ser Thr Thr Pro Tyr Asp Met Val Arg Val Asn Asn Ile
            740                 745                 750

Asp Arg Tyr Glu Leu Gln Ala Glu Ala Leu Arg Met Ile Asp Ala Asp
        755                 760                 765

Lys Tyr Ala Asp Lys Ile Asn Glu Leu Glu Ala Phe Arg Gln Glu Ala
770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Asn Lys Gln Gly Ala Ile Ser Ala
                805                 810                 815

Thr Ala Ala Thr Ala Gly Asp Asn Glu
            820                 825
```

<210> SEQ ID NO 25
<211> LENGTH: 2367
<212> TYPE: DNA
<213> ORGANISM: Lactobacillus pentosus

<400> SEQUENCE: 25

```
atgtctacag attactcatc accagcatat ttgcaaaaag ttgataagta ctggcgtgct    60
gccaactatt tatcagttgg tcaactttat ttaaaagata tcctttatt acaacggcca    120
ttaaaggcta gtgacgttaa ggttcaccca atcggtcact ggggcacgat tgccggccaa    180
aacttcatct atgcgcatct taaccgggtc atcaacaagt acggtttgaa gatgttctac    240
gttgaaggtc caggtcatgg tggccaagtg atggtctcca actcataccct tgatgggact    300
tacacggata tttatcctga aattacgcag atgttgaag ggatgcaaaa actcttcaag    360
caattctcat tcccaggtgg cgtggcttcc catgctgctc ctgaaacacc aggctcaatc    420
cacgaaggtg cgaacttggt ttactcaatt tcacacggtg ttggggcaat ccttgacaac    480
cctgatgaaa tcgccgcagt cgttgttggt gatgggaat ccgaaaccgg cccattagca    540
acttcatggc aatcaacgaa gttcatcaac ccaatcaacg atgggcagt gttaccaatc    600
ttgaacctta acggctttaa gatttctaac ccaacgattt ttggtcggac ttctgatgaa    660
aagatcaagc aatacttcga aagcatgaac tgggaaccaa tctttgttga aggtgacgat    720
cctgaaaagg ttcacccagc tttagctaag gccatggatg aagccgtcga aaagatcaaa    780
gccattcaaa agaacgctcg tgaaaacgat gacgctactt taccagtatg gccgatgatc    840
```

```
gtcttccgcg cacctaaggg ctggactggt cctaagtcat gggatggcga caagatcgaa    900
ggttcattcc gagctcacca aattccaatt cctgttgacc aaaccgacat ggaacatgcc    960
gatgcgttag ttgactggtt ggaatcatat caaccaaagg aactcttcaa tgaagatggt   1020
tctttgaagg atgatatcaa agaaattatc ccaactggcg atgcacggat ggccgctaac   1080
ccaatcacta atggtggggt tgatccaaag gccttgaact acctaacttc cgtgattac    1140
gccgttgata cgtctaagca tggtgccaac gttaagcaag atatgatcgt ttggtcagac   1200
tacttgcgtg atgttatcaa gaagaaccca gataacttcc ggttatttgg ccctgatgaa   1260
accatgtcaa accggttata tggtgtcttt gaaaccacta accgtcaatg gatggaagat   1320
attcacccag atagtgacca atacgaagca cctgctggcc gggtcttgga tgctcaatta   1380
tctgaacacc aagctgaagg ttggttagaa ggttacgtct taactggtcg tcatggcttg   1440
tttgcaagtt acgaagcctt cttacgggtt gtcgactcaa tgttgacgca acacttcaag   1500
tggttacgta aggccaacga acttgactgg cggaagaagt acccgtcact caacattatc   1560
gcggcttcaa ctgtgttcca acaagaccat aatgggtaca cccaccaaga tccaggtgcc   1620
ttgactcatt tggctgaaaa gaagcctgaa tatatccgcg aatatttacc agccgacgcc   1680
aactccttgt tagctgttgg ggacgtcatc ttccgtagcc aagaaaagat caactacgtg   1740
gttacgtcga agcacccacg tcaacaatgg ttcagcattg aagaagctaa gcaattagtt   1800
gacaacggtc ttggtatcat tgactgggca agcacggacc aaggtagcga accagatatc   1860
gtgtttgctg ctgccggaac ggaaccaacg cttgaaacgt tggctgcaat ccaattgctc   1920
catgatagct tcccagacat gaagattcgt ttcgtgaacg tggtcgacat cttgaagtta   1980
cgtagccctg aaaaggaccc tcgtggcttg tcagatgctg aatttgacca ttacttcact   2040
aaggacaaac cagttgtctt cgccttccat ggttacgaag acctggttcg tgacatcttc   2100
tttgatcgtc acaaccacaa cttacacgtg catggctacc gtgaaaatgg tgacattacg   2160
acaccattcg atgtccgggt catgaaccaa atggaccgtt cgacttagc aaaatctgca   2220
attgcggcgc aaccagcaat ggaaaacacc ggtgcagcct ttgttcaaga catggataac   2280
atgcttgcaa acacaacgc atacatccgt gacgccggaa ccgacttgcc agaagttaac   2340
gactggcaat ggaaaggttt gaaataa                                       2367
```

<210> SEQ ID NO 26
<211> LENGTH: 788
<212> TYPE: PRT
<213> ORGANISM: Lactobacillus pentosus

<400> SEQUENCE: 26

Met Ser Thr Asp Tyr Ser Ser Pro Ala Tyr Leu Gln Lys Val Asp Lys
1               5                   10                  15

Tyr Trp Arg Ala Ala Asn Tyr Leu Ser Val Gly Gln Leu Tyr Leu Lys
            20                  25                  30

Asp Asn Pro Leu Leu Gln Arg Pro Leu Lys Ala Ser Asp Val Lys Val
        35                  40                  45

His Pro Ile Gly His Trp Gly Thr Ile Ala Gly Gln Asn Phe Ile Tyr
    50                  55                  60

Ala His Leu Asn Arg Val Ile Asn Lys Tyr Gly Leu Lys Met Phe Tyr
65                  70                  75                  80

Val Glu Gly Pro Gly His Gly Gly Gln Val Met Val Ser Asn Ser Tyr
                85                  90                  95

Leu Asp Gly Thr Tyr Thr Asp Ile Tyr Pro Glu Ile Thr Gln Asp Val

-continued

```
               100                 105                 110
Glu Gly Met Gln Lys Leu Phe Lys Gln Phe Ser Phe Pro Gly Gly Val
           115                 120                 125
Ala Ser His Ala Ala Pro Glu Thr Pro Gly Ser Ile His Glu Gly Gly
           130                 135                 140
Glu Leu Gly Tyr Ser Ile Ser His Gly Val Gly Ala Ile Leu Asp Asn
145                 150                 155                 160
Pro Asp Glu Ile Ala Ala Val Val Gly Asp Gly Glu Ser Glu Thr
                        165                 170                 175
Gly Pro Leu Ala Thr Ser Trp Gln Ser Thr Lys Phe Ile Asn Pro Ile
                    180                 185                 190
Asn Asp Gly Ala Val Leu Pro Ile Leu Asn Leu Asn Gly Phe Lys Ile
                195                 200                 205
Ser Asn Pro Thr Ile Phe Gly Arg Thr Ser Asp Glu Lys Ile Lys Gln
            210                 215                 220
Tyr Phe Glu Ser Met Asn Trp Glu Pro Ile Phe Val Glu Gly Asp Asp
225                 230                 235                 240
Pro Glu Lys Val His Pro Ala Leu Ala Lys Ala Met Asp Glu Ala Val
                    245                 250                 255
Glu Lys Ile Lys Ala Ile Gln Lys Asn Ala Arg Glu Asn Asp Asp Ala
                260                 265                 270
Thr Leu Pro Val Trp Pro Met Ile Val Phe Arg Ala Pro Lys Gly Trp
            275                 280                 285
Thr Gly Pro Lys Ser Trp Asp Gly Asp Lys Ile Glu Gly Ser Phe Arg
        290                 295                 300
Ala His Gln Ile Pro Ile Pro Val Asp Gln Thr Asp Met Glu His Ala
305                 310                 315                 320
Asp Ala Leu Val Asp Trp Leu Glu Ser Tyr Gln Pro Lys Glu Leu Phe
                    325                 330                 335
Asn Glu Asp Gly Ser Leu Lys Asp Ile Lys Glu Ile Ile Pro Thr
                340                 345                 350
Gly Asp Ala Arg Met Ala Ala Asn Pro Ile Thr Asn Gly Gly Val Asp
            355                 360                 365
Pro Lys Ala Leu Asn Leu Pro Asn Phe Arg Asp Tyr Ala Val Asp Thr
        370                 375                 380
Ser Lys His Gly Ala Asn Val Lys Gln Asp Met Ile Val Trp Ser Asp
385                 390                 395                 400
Tyr Leu Arg Asp Val Ile Lys Lys Asn Pro Asp Asn Phe Arg Leu Phe
                    405                 410                 415
Gly Pro Asp Glu Thr Met Ser Asn Arg Leu Tyr Gly Val Phe Glu Thr
                420                 425                 430
Thr Asn Arg Gln Trp Met Glu Asp Ile His Pro Asp Ser Asp Gln Tyr
            435                 440                 445
Glu Ala Pro Ala Gly Arg Val Leu Asp Ala Gln Leu Ser Glu His Gln
        450                 455                 460
Ala Glu Gly Trp Leu Glu Gly Tyr Val Leu Thr Gly Arg His Gly Leu
465                 470                 475                 480
Phe Ala Ser Tyr Glu Ala Phe Leu Arg Val Val Asp Ser Met Leu Thr
                    485                 490                 495
Gln His Phe Lys Trp Leu Arg Lys Ala Asn Glu Leu Asp Trp Arg Lys
                500                 505                 510
Lys Tyr Pro Ser Leu Asn Ile Ile Ala Ala Ser Thr Val Phe Gln Gln
            515                 520                 525
```

```
Asp His Asn Gly Tyr Thr His Gln Asp Pro Gly Ala Leu Thr His Leu
530                 535                 540

Ala Glu Lys Lys Pro Glu Tyr Ile Arg Glu Tyr Leu Pro Ala Asp Ala
545                 550                 555                 560

Asn Ser Leu Leu Ala Val Gly Asp Val Ile Phe Arg Ser Gln Glu Lys
                565                 570                 575

Ile Asn Tyr Val Val Thr Ser Lys His Pro Arg Gln Gln Trp Phe Ser
                580                 585                 590

Ile Glu Glu Ala Lys Gln Leu Val Asp Asn Gly Leu Gly Ile Ile Asp
            595                 600                 605

Trp Ala Ser Thr Asp Gln Gly Ser Glu Pro Asp Ile Val Phe Ala Ala
610                 615                 620

Ala Gly Thr Glu Pro Thr Leu Glu Thr Leu Ala Ala Ile Gln Leu Leu
625                 630                 635                 640

His Asp Ser Phe Pro Asp Met Lys Ile Arg Phe Val Asn Val Val Asp
                645                 650                 655

Ile Leu Lys Leu Arg Ser Pro Glu Lys Asp Pro Arg Gly Leu Ser Asp
                660                 665                 670

Ala Glu Phe Asp His Tyr Phe Thr Lys Asp Lys Pro Val Val Phe Ala
            675                 680                 685

Phe His Gly Tyr Glu Asp Leu Val Arg Asp Ile Phe Phe Asp Arg His
690                 695                 700

Asn His Asn Leu His Val His Gly Tyr Arg Glu Asn Gly Asp Ile Thr
705                 710                 715                 720

Thr Pro Phe Asp Val Arg Val Met Asn Gln Met Asp Arg Phe Asp Leu
                725                 730                 735

Ala Lys Ser Ala Ile Ala Ala Gln Pro Ala Met Glu Asn Thr Gly Ala
                740                 745                 750

Ala Phe Val Gln Asp Met Asp Asn Met Leu Ala Lys His Asn Ala Tyr
            755                 760                 765

Ile Arg Asp Ala Gly Thr Asp Leu Pro Glu Val Asn Asp Trp Gln Trp
770                 775                 780

Lys Gly Leu Lys
785

<210> SEQ ID NO 27
<211> LENGTH: 2478
<212> TYPE: DNA
<213> ORGANISM: Artificial Sequence
<220> FEATURE:
<223> OTHER INFORMATION: codon optimized xfp gene of B.
      animalis(xfp01ec)

<400> SEQUENCE: 27
atgacaaatc ccgtaatagg aaccccctgg cagaaactgg atcgtccggt aagcgaggaa      60
gcgattgagg gcatggataa atattggcgc gtggcgaact atatgagcat ggccagatt     120 tatctgcgtt cgaacccgct gatgaaagaa cccttaccc gcgacgatgt gaaacatcgt     180
ctggtgggcc attggggcac caccccgggc ctgaactttc tactggcgca cattaaccgc     240
ctgattgcgg accatcagca gaacaccgtg tttattatgg acccggcca tggcggcccc     300 gctggaaccg ctcagagcta tattgatggc acctataccg aatattatcc gaacattacc     360
aaagatgaag ctggcctgca gaatttttt cgccagttta gctatccggg aggcataccc     420
agccattttg ctccggaaac gcccggcagc attcatgagg gcggcgaact gggctatgcg     480
```

```
ctgagccatg cgtatggcgc cattatgaac aacccgtcgc tgtttgtgcc gtgcattatt    540
ggagatggcg aggcggaaac cggcccctg gcgaccggct ggcagagcaa caaactggtg    600
aacccgcgca ccgatggcat tgtgctgccg attctgcatc tgaacggcta taaaattgcg    660
aacccgacgc tgctggcgcg cattagcgat gaagaactgc atgatttttt tcgcggaatg    720
ggatatcatc cgtatgaatt tgtggcgggc tttgataacg aagaccatct gagcattcat    780
cgtcgctttg cggaactgtt tgaaaccatt tttgatgaaa tttgcgacat taaagctgcc    840
gctcagaccg atgatatgac ccgtccgttt tatccgatgc tgattttcg caccccgaaa    900
ggctggacct gcccgaaatt tattgatggc aaaaaaaccg agggcagctg gcgtgctcat    960
caggtgccgc tggctagcgc gcgcgatacc gaagcgcatt ttgaggtgct gaaaggctgg   1020
atggagagct ataaaccgga gaactgtttt aacgcggatg gcagcattaa agatgatgtg   1080
accgctttta tgcccaaagg cgagctgcgc attggcgcga cccgaacgc gaacggaggc   1140
cgcattcgcg aagacctgaa actgcccgaa ctggaccagt atgaaattac cggcgtgaaa   1200
gagtatggcc acggctgggg ccaggtggaa gctccgcgca gcctgggcgc ctattgccgc   1260
gatattatta aaacaacccc ggacagcttt cgcattttg ggcccgacga aaccgctagc   1320
aaccgtctga cgccaccta tgaagtgacc aaaaaaacagt gggataacgg ctacctgagc   1380
gctctggtgg atgaaaacat ggctgtgacc ggccaggtag tggaacagct gagcgaacac   1440
cagtgcgagg gctttctgga agcgtatctg ctgacgggcc ccatggcat gtggtcgacc   1500
tacgaaagct ttgcgcatgt gattgatagc atgctgaacc agcacgccaa atggctggaa   1560
gccaccgtgc gcgaaattcc gtggcgcaaa ccgattagca gcgtgaacct gctggtgagc   1620
agccatgtgt ggcgtcagga tcataacggc tttagccacc aggatccggg agtgaccagc   1680
gtgctgatta caaaaacgtt taacaacgat catgtgacga acatttattt tgccaccgat   1740
gcgaacatgc tgctggccat tgcggaaaaa tgctttaaaa gcaccaacaa aattaacgcc   1800
atttttagcg gcaaacagcc ggctccgacc tggataaccc tggatgaagc tcgagcggaa   1860
ctggaagcgg gcgcggcgga atggaaatgg gctagcaacg cgaaatcgaa cgatgaagtg   1920
cagatagtgc tggcggcggc tggcgacgtg ccgacccagg aaattatggc ggctagcgac   1980
gcgctgaaca aagacggcat taaatttaaa gtggtgaacg tagtagatct gctgaaactg   2040
cagagcccgg aaaacaacga tgaagcgatg agcaacgagg attttaccga actgtttacc   2100
gcggataagc cggtactgtt tgcgtatcat agctacgcgc aggatgtacg tggactaatt   2160
tatgatcgcc cgaaccatga taactttaac gtagtgggct ataaagaaca gggcagcacg   2220
accacgccgt ttgatatggt gcgcgtgaac gatatggacc gctatgccct ggaggctcag   2280
gctctggaac tgattgatgc ggataaatac gcggataaaa ttgatgaact gaacgccttt   2340
cgcaaaaccg cctttcagtt tgcggtggat aacggctatg atattccgga atttaccgat   2400
tgggtgtatc cggatgtgaa agtggatgaa acgcagatgc tgagcgccac cgccgccacc   2460
gctggcgata acgaataa                                                 2478
```

<210> SEQ ID NO 28
<211> LENGTH: 2478
<212> TYPE: DNA
<213> ORGANISM: Artificial Sequence
<220> FEATURE:
<223> OTHER INFORMATION: codon optimized fxpk gene of B. adolescentis(fxpk01ec)

<400> SEQUENCE: 28

```
atgacgtctc cgtaataggc acccccctgg aaaaaactga acgctccggt aagcgaagag    60
gctattgagg gcgtggacaa atattggcgc gctgcgaact atctgagcat tggccagatt   120
tacctgcgta gcaacccgct gatgaaagaa ccctttaccc gcgaggatgt gaaacatcgt   180
ctggtgggac attggggcac cacccccggc ctgaactttc tgattggcca tattaaccgt   240
ctgatagctg accatcagca gaacacagtg attattatgg gcccgggcca tggcggcccg   300
gctggaaccg ctcagagcta tctggatggc acctataccg aatattttcc gaacattacc   360
aaagacgaag ctggcctgca gaattttttt cgccagttta gctatccggg aggcattccg   420
agccattatg ctccggaaac cccgggcagc attcatgagg gcggcgaact gggatatgcg   480
ctgagccatg cgtatggcgc tgtgatgaac aacccgtcgc tgtttgtgcc ggcgattgtg   540
ggcgatggag aggctgaaac cggcccgctg gcgaccggct ggtttagcaa caaactgatt   600
aacccgcgca ccgatggaat tgtgctgccg attctgcatc tgaacggcta taaaattgcg   660
aacccgacca ttctgagccg cattagcgat gaggaactgc atgaatttttt tcatggcatg   720
ggctacgaac cgtatgaatt tgtggctggc tttgataacg aagaccatct gtcgattcat   780
cgtcgttttg cggaactgtt tgaaaccgtg tttgatgaaa tttgcgatat taaagcggcg   840
gctcagaccg atgatatgac acgtccgttt tatccgatga ttattttcg tacccccgaaa   900
ggctggacct gcccgaaatt tattgatggc aaaaaaaccg aaggcagctg gcgtagccat   960
caggtgccgc tggctagcgc gcgcgacacc gaagcgcatt ttgaagtgct gaaaaactgg  1020
ctggaaagct ataaaccgga ggaactgttt gatgaaaacg gcgcggtgaa accggaggtg  1080
accgcgtttta tgccgaccgg cgagctgcgc attggagaaa acccgaacgc gaacggaggc  1140
cgcattcgcg aggaactgaa actgccgaaa ctggaggatt atgaagtgaa agaggtggcg  1200
gaatatggcc atggctgggg ccagctgaaa gcgacccgtc gtctgggcgt gtataccccgc  1260
gatattatta aaaacaaccc ggatagcttt cgtattttttg ggccggacga aaccgctagc  1320
aaccgtctgc aggcggctta tgatgtgacc aacaaacagt gggatgcggg ctatctgagc  1380
gctcaggtgg atgaacacat ggctgtgacc ggccaggtga ccgaacagct aagcgaacat  1440
cagatggagg gctttctgga aggctatctg ctgaccggcc gtcatggcat ttggagcagc  1500
tacgaaagct ttgtgcatgt gattgatagc atgctgaacc agcatgcgaa atggttagaa  1560
gctaccgtgc gcgaaatacc gtggcgcaaa ccgattagca gcatgaacct gctggtgagc  1620
agccatgtgt ggcgtcagga ccataacggc tttagccatc aggacccggg agtgaccagc  1680
gtgctgctga acaaatgctt taacaacgac catgtgattg catttatttt tccggtggac  1740
agcaacatgc tgttagctgt ggctgaaaaa tgctataaaa gcaccaacaa aattaacgcg  1800
attattgcgg gcaaacagcc ggcggcgacc tggctgaccc tggatgaggc tcgcgcggaa  1860
ctggaaaaag gagctgcgga atggaaatgg gctagcaacg tgaaaagcaa cgacgaagct  1920
cagattgtgc tggcggcgac cggagacgta ccgacacagg agattatggc ggctgcggat  1980
aaactggatg cgatgggcat taaatttaaa gtggtgaacg tggtagatct ggtgaaactg  2040
cagagcgcga agaaaacaa cgaagcgctg agcgacgaag aatttgctga actgtttacc  2100
gaagataaac cggtgctgtt tgcttatcat agctacgcgc gcgacgtgcg tggactgatt  2160
tatgaccgcc cgaaccatga aactttaac gtacatggct atgaagaaca gggcagcacc  2220
accacccccgt atgatatggt acgcgtgaac aacattgacc gctatgaatt acaggctgag  2280
gctctgcgca tgatagatgc tgataaatat gcggataaaa ttaacgaact ggaagcgttt  2340
cgtcaggagg cgtttcagtt tgctgtggat aacggctatg accatccgga ctataccgat  2400
```
tgggtgtata gcggagtgaa caccaacaaa cagggagcta ttagcgctac cgcggctacc    2460
gctggcgaca acgaataa                                                  2478

<210> SEQ ID NO 29
<211> LENGTH: 2367
<212> TYPE: DNA
<213> ORGANISM: Artificial Sequence
<220> FEATURE:
<223> OTHER INFORMATION: codon optimized xpk gene of L. pentosus
      (xpk01ec)

<400> SEQUENCE: 29
atgtctacag attatagcag cccggcatac ctgcagaagg tggataaata ttggcgcgcg     60
gccaactacc tgagcgtggg ccagctttac ctgaaggata tcctctgct gcagcgcccg     120 ctgaaagcct cggacgtgaa agtgcatccg attggccatt ggggtaccat tgccggtcag    180
aactttattt acgctcacct taaccgcgtt attacaaat atggcctgaa atgtttat       240 gtggaaggcc cgggccacgg cggtcaggta atggtttcta cagctatct tgatggaacg    300 tataccgata tttaccctga aattacccaa gatgtggaag gaatgcagaa gctcttaaaa    360
cagtttagct ttccgggcgg tgtagcctct cacgccgccc ctgaaacacc gggtagcatt    420
catgaaggcg gtgaacttgg ctatagcatt agccatggcg tgggagcaat tcttgacaac    480
cctgatgaaa ttgccgcagt tgtggtgggc gatggagaat ctgaaacggg tccgctggca    540
acgagctggc agagcaccaa atttattaac ccgattaacg atggagcagt actgccgatt    600
ctgaacctta cgtttcaa aatttctaac ccgaccattt tcggccgcac gtctgatgaa    660
aaaattaaac agtatttga atctatgaac tgggaaccga tttcgtgga aggcgacgat    720 cctgaaaaag tgcatccggc cctggccaaa gccatggatg aagccgttga aaaaattaag    780
gccattcaga aaacgcccg cgaaaacgat gacgccacgc tgccggtatg gcccatgatt    840 gttttcgag cacctaaagg ttggacgggc cctaaaagct gggatggtga caaaattgaa    900
ggcagcttta gggcccatca gattccgatt ctgtggaccc agacggacat ggaacacgcc    960
gatgctctgg tggactggct ggaaagctac cagccgaaag aactctttaa tgaagatggc    1020
tctctgaaag atgatattaa ggaaattatt ccgacgggtg atgcacgcat ggccgccaac    1080
ccgattacga atgcggagt ggatccgaaa gccctgaacc tgcctaactt cgcgattat      1140 gccgtggata cctctaaaca cggcgccaac gtgaaacagg atatgattgt gtggagcgac    1200
tatctgcgcg atgtgattaa aaaaaacccg gataactttc gcctgttcgg tcctgatgaa    1260
acgatgagca accgcctgta cggcgttttc gaaacgacga accgccagtg gatggaagat    1320
attcatccgg attcggacca gtatgaagca cctgccggtc gcgttctgga tgcccagctg    1380
tctgaacatc aggccgaagg ctggctggaa ggctatgttc tgacgggccg ccacggtctg    1440
ttcgcatcgt atgaagcctt tctgcgcgtg gttgacagca tgctgaccca gcattttaaa    1500
tggctgcgca aagccaacga acttgactgg cgcaaaaaat atcccagcct caacattatt    1560
gctgccagca cggtatttca gcaggaccac aatggatata cgcatcagga tccgggcgcc    1620
ctgacgcacc tggccgaaaa aaaacctgaa tacattcgag aatacctgcc ggccgacgcc    1680
aactctctgc tggccgtggg agacgttatt tttcgctctc aggaaaaaat taactatgta    1740
gtgacctcta acatccgcgc ccagcagtgg ttttctattg aagaagccaa acagctggtg    1800
gacaacggcc ttggcattat tgactggca tctaccgacc agggctctga accggatatt    1860
gtattcgccg ccgccgggac cgaaccgacc cttgaaaccc tggccgcaat tcagctgctc    1920

```
cacgattctt ttccggacat gaaaattcgc tttgtaaacg tagttgacat tctgaaactg      1980
cgctctcctg aaaaagaccc tcgcggtctg agcgatgccg aatttgacca ctattttacg      2040
aaagacaagc cggtggtttt tgcctttcac ggctatgaag acctcgtgcg cgacattttt      2100
ttcgatcgcc ataaccataa cctgcatgta cacggttatc gcgaaaatgg cgacattacc      2160
acaccgtttg atgttcgcgt tatgaaccag atggaccgct ttgacctggc aaagtctgca      2220
attgctgctc agccggcaat ggaaaacacg ggcgcagcct tcgtgcagga catggataac      2280
atgcttgcaa agcataacgc atatattcgc gacgccggga cggacctgcc ggaagtgaac      2340
gactggcagt ggaagggcct gaagtaa                                          2367
```